United States Patent
Doyle, III et al.

(10) Patent No.: US 7,651,845 B2
(45) Date of Patent: Jan. 26, 2010

(54) METHOD AND APPARATUS FOR GLUCOSE CONTROL AND INSULIN DOSING FOR DIABETICS

(75) Inventors: Francis J. Doyle, III, Santa Barbara, CA (US); Lois Jovanovic, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/129,033

(22) Filed: May 12, 2005

(65) Prior Publication Data

US 2005/0272640 A1    Dec. 8, 2005

Related U.S. Application Data

(60) Provisional application No. 60/571,247, filed on May 13, 2004.

(51) Int. Cl.
*C12Q 1/54* (2006.01)
(52) U.S. Cl. ...................................................... 435/14
(58) Field of Classification Search ........................ None
See application file for complete search history.

(56) References Cited

U.S. PATENT DOCUMENTS

| | | | |
|---|---|---|---|
| 4,731,726 A | * | 3/1988 | Allen, III ..................... 600/300 |
| 5,411,889 A | * | 5/1995 | Hoots et al. ..................... 436/6 |
| 5,468,727 A | | 11/1995 | Phillips et al. |
| 6,544,212 B2 | | 4/2003 | Galley et al. |
| 6,554,798 B1 | | 4/2003 | Mann |

OTHER PUBLICATIONS

Bequette et al. "Intelligent Dosing System": Need for Design and Analysis Based on Control Theory, Diabetes Technology and Therapeutics, vol. 6, No. 6, pp. 868-873.
Doyle III, F.J.; Srinivasan, B.; Bonvin, D. Run-to-Run control strategy for diabetes managment, Proceedings of the 23rd Anual EMBS International Conference, Istambul, Turkey, Oct. 2001.
Jovanovic, Lois. Insulin therapy and algorithms for treating type 1 diabetes mellitus, in Optimizing insulin therapy in patients with diabetes (monograph), 2003, pp. 13-19.
Parker, Robert S.; Doyle III, Francis J.; Peppas, Nicholas A. A model-based algorithm for blood glucose control in type il diabetic patients. IEEE Transactions on Biomedical Engineering, vol. 46, No. 2, Feb. 1999, pp. 148-157.

* cited by examiner

*Primary Examiner*—Sandra Saucier
*Assistant Examiner*—Satyendra K Singh
(74) *Attorney, Agent, or Firm*—John P. O'Banion

(57) ABSTRACT

A computer implemented method and associated apparatus for the combined control of insulin bolus dosing and basal delivery for the goal of achieving normal glycemic response to meals, exercise, stressors, and other perturbations to blood glucose levels. A run-to-run algorithm is used to monitor blood glucose levels and adjust insulin delivery as conditions are varied.

21 Claims, 16 Drawing Sheets

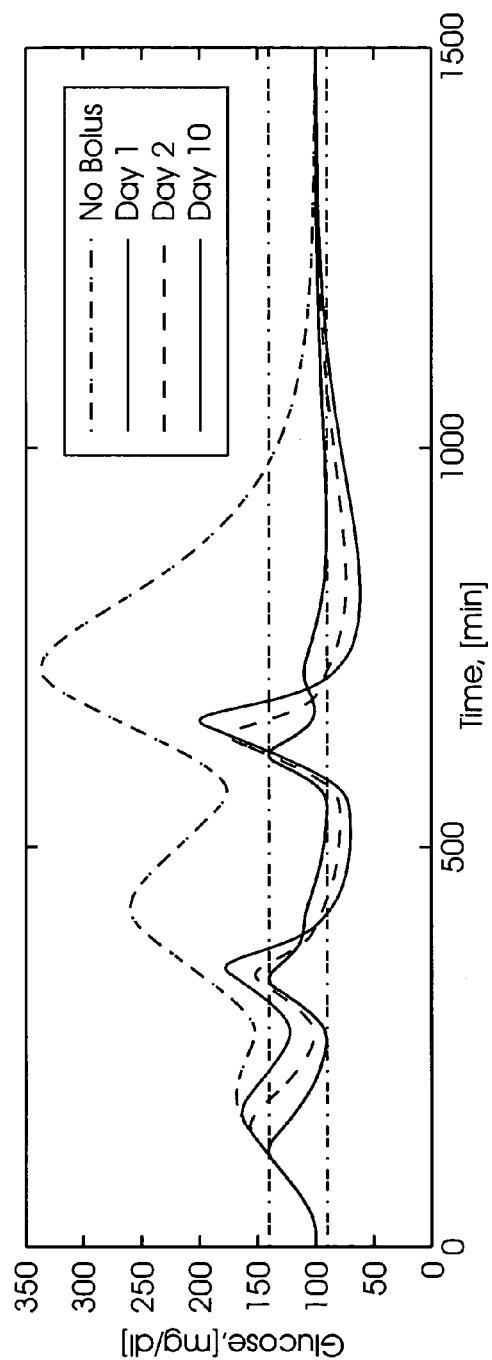
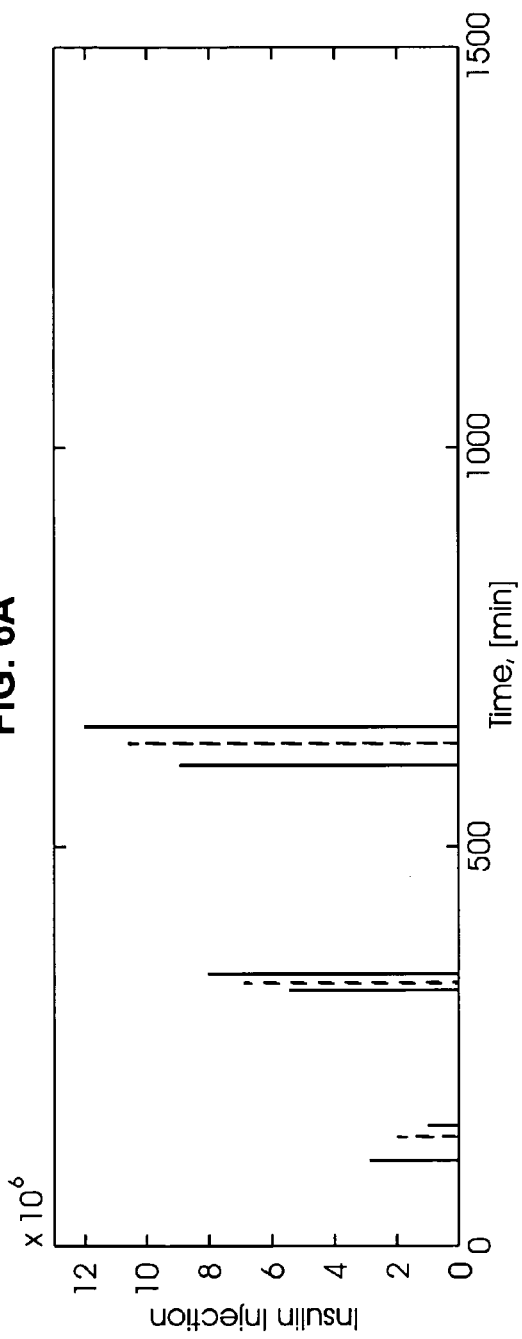
FIG. 6A
FIG. 6B

METHOD AND APPARATUS FOR GLUCOSE CONTROL AND INSULIN DOSING FOR DIABETICS

CROSS-REFERENCE TO RELATED APPLICATIONS

This application claims priority from U.S. provisional application Ser. No. 60/571,247 filed on May 13, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to management of glucose and insulin delivery levels to mimic a natural beta cell, and more particularly, to an apparatus and method using a run-to-run algorithm for episodic basal and bolus insulin dosing and monitoring of plasma glucose levels.

2. Incorporation by Reference of Publications

The following publications referenced herein using numbers inside brackets (e.g., [1]) are incorporated by reference herein in their entirety:

[1] T. Mandrup-Poulsen, "Recent advances: Diabetes," Br. Med. J., vol. 316, pp. 1221-1225, April 1998.

[2] American Diabetes Association, "Standards of medical care for patients with diabetes mellitus," Diabetes Care, vol. 26, pp. S33-S50, 2003.

[3] Diabetes Control and Complications Trial Research Group, "The effect of intensive treatment of diabetes on the development and progression of long-term complications in insulin-dependent diabetes mellitus," N. Engl. J. Med., vol. 329, pp. 977-986, September 1993.

[4] American Diabetes Association, "Standards of medical care for patients with diabetes mellitus," Diabetes Care, vol. 26, pp. S33-S50, January 2003.

[5] L. Jovanovic and C. Peterson, "Home blood glucose monitoring," Comp. Ther., vol. 8, pp. 10-20, January 1982.

[6] L. Chanoch, L. Jovanovic, and C. Peterson, "The evaluation of a pocket computer as an aid to insulin dose determination by patients," Diabetes Care, vol. 8, pp. 172-176, March/April 1982.

[7] A. Schiffrin, M. Mihic, B. Leibel, and A. Albisser, "Computer-assisted insulin dosage adjustment," Diabetes Care, vol. 8, pp. 545-552, November/December 1985.

[8] F. Chiarelli, S. Tumini, G. Morgese, and A. Albisser, "Controlled study in diabetic children comparing insulin-dosage adjustment by manual and computer algorithms," Diabetes Care, vol. 13, pp. 1080-1084, 1990.

[9] C. Mao, M. Riegelhuth, D. Gundy, C. Cortez, S. Melendez, and E. Ipp, "An overnight insulin infusion algorithm provides morning normoglycemia and can be used to predict insulin requirements in noninsulin-dependent diabetes mellitus," J. Clin. Endo. Metab., vol. 82, pp. 2466-2470, April 1997.

[10] A. Albisser, "Toward algorithms in diabetes self-management," Diab. Tech. Ther., vol. 5, pp. 371-373, 2003.

[11] J. Moyne, E. del Castillo, and A. Hurwitz, Run-to-run Control in Semiconductor Manufacturing. New York, N.Y.: CRC Press, 2001.

[12] K. Lee, I. Chin, and H. Lee, "Model predictive control technique combined with iterative learning for batch processes," AIChE J., vol. 45, pp. 2175-2187, 1999.

[13] R. Bergman, L. Phillips, and C. Cobelli, "Physiologic evaluation of factors controlling glucose tolerance in man," J. Clin. Invest., vol. 68, pp. 1456-1467, 1981.

[14] R. Bergman, Y. Ider, C. Bowden, and C. Cobelli, "Quantitative estimation of insulin sensitivity," Am. J. Physiol., vol. 236, pp. E667-E677, 1979.

[15] J. Sorensen, "A physiologic model of glucose metabolism in man and its use to design and assess improved insulin therapies for diabetes," Ph.D. dissertation, Massachusetts Institute of Technology, Boston, 1985.

[16] R. Parker and F. Doyle III, "Control-relevant modeling in drug delivery," Adv. Drug Deliv. Rev., vol. 48, pp. 211-228, 2001.

[17] M. Berger and D. Rodbard, "Computer simulation of plasma insulin and glucose dynamics after subcutaneous insulin injection," Diabetes Care, vol. 12, pp. 725-736, November/December 1989.

[18] S. Arimoto, S. Kawamura, and F. Miyazaki, "Bettering operation of dynamic systems by learning: A new control theory for servomechanism or mechatronics systems," in Proc. IEEE 23rd Conference on Decision and Control, Las Vegas, Nev., Dec. 1984, pp. 1064-1069.

[19] N. Amann, D. Owens, and E. Rogers, "Iterative learning control for discrete-time systems with exponential rate of convergence," in Proc. IEE Control Theory Appl., Dearborn, Mich., March 1996, pp. 217-224.

[20] K. Lee, S. Bang, and K. Chang, "Feedback-assisted iterative learning control based on an inverse process model," J. Proc. Cont., vol. 4, pp. 77-89, May 1994.

[21] J. Lee, K. Lee, and W. Kim, "Model-based iterative learning control with a quadratic criterion for time-varying linear systems," Automatica, vol. 36, pp. 641-657, May 2000.

[22] B. Srinivasan, C. Primus, D. Bonvin, and N. Ricker, "Run-to-run optimization via control of generalized constraints," Contr. Eng. Prac., vol. 9, pp. 911-919, 2001.

[23] B. Srinivasan, S. Palanki, and D. Bonvin, "Dynamic optimization of batch process. I. Characterization of the nominal solution," Comp. Chem. Eng., vol. 27, pp. 1-26, 2002.

[24] B. Srinivasan, D. Bonvin, E. Visser, and S. Palanki, "Dynamic optimization of batch processes. II. Role of measurements in handling uncertainty," Comp. Chem. Eng., vol. 27, pp. 27-44, 2002.

[25] Cook C B, Mann L J, King E C, New K M, Vaughn P S, Dames F D, Dunbar V G, Caudle J M, Tsui C, George C D, McMichael J P: Management of insulin therapy in urban diabetes patients is facilitated by use of an intelligent dosing system. Diabetes Technol Ther 2004; 6:326-335.

[26] Gopakumaran B: Intelligent dosing system: a useful computer program for diabetic management? Diabetes Technol Ther 2004; 6:336-338.

[27] Gross T, Kayne D, King A, Rother C, Juth S: A bolus calculator is an effective means of controlling postprandial glycemia in patients on insulin pump therapy. Diabetes Technol. Ther. 2003; 5:365-369.

3. Description of Related Art

Diabetes mellitus affects over 100 million individuals worldwide, and this number is expected to double by 2010 [1]. In the US, the estimated healthcare costs of the 12 million affected is estimate to be 136 billion dollars annually. Diabetes mellitus is a disorder of the metabolism that is characterized by the inability of the pancreas to secrete sufficient amounts of insulin [2]. Insufficient amounts of insulin results in large fluctuations in blood glucose levels can have both short-term and long-term physiological consequences. Long-term complications arising from elevated blood glucose levels (hyperglycemia) in patients with Type 1 diabetes include retinopathy, neuropathy, nephropathy and other vascular complications. Low glucose levels (hypoglycemia) can lead to diabetic coma, seizures, accidents, anoxia, brain damage, decreased cognitive function, and death.

The conventional approach to glucose regulation in diabetic patients includes 3-5 daily insulin injections, with the quantity of insulin being determined by 4-8 invasive blood glucose measurements each day. This method of insulin delivery is painful, inconvenient and may be unreliable due to the pharmacokinetics of the insulin analogues that are typically used. Pen devices have been developed to make insulin delivery more convenient; however, the inability to mix insulin or insulin analogue types is a disadvantage. Several other routes of insulin delivery have been studied as an alternative to insulin injections including inhalation and transdermal insulin delivery. Others have explored the efficacy of continuous subcutaneous insulin infusion (CSII) using a pump. This has mainly been done in comparison to conventional insulin therapy or multiple daily insulin injections (MDI). Continuous subcutaneous insulin infusions by external insulin infusion pumps normally use rapid-acting insulin analogues.

Typical fixed dosage approaches assume that the metabolic demands of each day are metabolically similar, and that the fixed dosages adequately anticipate the timing and quantity of insulin that is required by the patient.

Unfortunately, blood glucose fluctuations continue to occur uncontrollably in many patients beyond the normal range of 60-120 mg/dl, exacerbating the risks of physical complications. Periodic episodes of hypoglycemia and hyperglycemia may occur when the insulin needs of the patient deviate from the levels predicted by regimen and present in the bloodstream.

The development of external insulin infusion pumps, along with the introduction of rapid acting insulin analogs has greatly aided in making intensive insulin therapy feasible. The efficacy of the insulin therapy is quantified by measurement of the percentage of glycosylated hemoglobin in the bloodstream (A1C). Values less than 6% are seen in normal healthy people without diabetes; whereas, higher percentages are indicative of sustained hyperglycemia [4].

Several algorithms have been developed to optimize the insulin therapy of people with diabetes. Jovanovic et al. proposed several insulin delivery logic rules for an NPH/Regular insulin system, a Lente insulin system and a constant subcutaneous insulin infusion system [5]. Heuristics were determined to account for food intake, weight loss, exercise, childhood, adolescence and pregnancy. Chanoch et al. evaluated the use of a pocket computer to aid in determining the proper insulin dose for people with diabetes [6]. Patient specific parameters such as weight, gender and physical activity along with carbohydrate content of meals and blood glucose measurements were used by the algorithm to optimize the insulin dose.

With use of the pocket computer, A1C values decreased from 7.2% to 5.8%, with a resulting mean blood glucose of 130 mg/dl versus 160 mg/dl before the study. Schiffren et al. also explored the use of computer algorithms for insulin dose adjustment [7]. Seven patients with type 1 diabetes were recruited to use the computer algorithm for an eight week period. During the control period, the mean blood glucose concentration for all patients was 178, 187, 208, and 207 mg/dl for breakfast, lunch, dinner and bedtime snack pre-meal measurements. Upon completion of the algorithm phase of the study, these values decreased to 116, 110, 148, and 135 mg/dl, respectively, for the same pre-meal measurements. Chiarelli et al. investigated the use of a computer algorithm in children [8]. Their results showed fewer episodes of hypoglycemia in the computer-assisted group. Other studies have employed the use of computer algorithms to maintain normal glycemia levels in patients with hyperglycemia, insulin-resistance and type 2 diabetes [9]. Albisser highlighted several algorithms that have been developed to aid in the progress of self-management of diabetes for better blood glucose control [10].

A number of virtual patient models for diabetes exist in the literature. The work that is described in the following sections emphasizes results evaluated on the Bergman model. In addition, the Sorensen and Automated Insulin Dosage Advisor (AIDA) models have been investigated, and those results are highlighted to emphasize the applicability of the run-to-run algorithm to different virtual patient systems.

The Bergman model is a three compartment minimal model of glucose and insulin dynamics [13]. This 3rd-order model is comprised of a glucose compartment, G, a remote insulin compartment, X, and an insulin compartment, I [14]. The remote insulin compartment mediates glucose uptake within the glucose space to the peripheral and hepatic tissues. The insulin distribution space combines the sinks and sources of insulin production and consumption into a single pool. While the Bergman model is simplistic in nature, it is able to capture certain dynamics of the diabetic patient system. The insulin dynamics of the Bergman model are driven by an intravenous infusion of insulin to the system.

The Sorensen model is a 6-compartment model [15], [16]. The compartments are physiological representations of the brain, heart and lungs, liver, gut, kidney and peripheral tissue. Within the brain and peripheral tissue, both the dynamics within the interstitial fluid and capillary fluid are detailed. The glucose meal disturbance is ingested directly into the gut accompanied by intravenous delivery of insulin and arterial blood glucose measurements. This 21st order model describes glucose, insulin and glucagon dynamics of the diabetic patient. Similar to the Bergman model, the Sorensen model relies on an intravenous infusion of insulin to drive the insulin dynamics of the system. Due to the incorporation of glucagon's action to promote hepatic output of glucose into the model, blood glucose levels do not remain in the hypoglycemic range for extended periods of time.

The Automated Insulin Dosage Advisor (AIDA) is a 4th-order 3-compartment model of insulin and glucose dynamics. In contrast to the Bergman model, the insulin dynamics of the model are driven by subcutaneous injection of insulin [17]. The AIDA model was first proposed as an educational tool.

Hence, the model does attempt to model the effects of different meal sizes on the rate of gastric emptying in the system. The AIDA model was also originally designed to reflect the use of several different insulin analogs on the insulin therapy of an individual. In doing so, subcutaneous transport dynamics were accounted for to simulate the effect of a subcutaneous injection of insulin to the body. The AIDA model was developed in the spirit of the minimal model approach, resulting in few patient specific parameters.

Run-to-run control (or batch) control has been commonly used in industrial batch processes, such as semiconductor manufacturing [11]. In run-to-run control, information about product quality from the previous run is used to determine the input for the next run [12].

Arimoto et al. proposed the "betterment process" concept as a measure of making the inputs for certain systems, such as mechanical robots, yield better outputs [18]. The concept can be applied to multi-input multi-output systems that have a repetitive or cyclic behavior. The convergence properties of this iterative learning control algorithm were studied by Amann et al. [19]. Using an inverse process model, Lee et al. derived a feedback-assisted iterative learning control scheme (FBALC) to attain the maximum convergence rate [20]. This approach was evaluated on a simulated bench-scale batch reactor, to demonstrate the ability of the algorithm to control reactor temperature. For time-varying linear constrained systems, prevalent in the chemical process control area, Lee et al. proposed a model-based iterative learning control scheme with a quadratic performance objective [21]. The feasibility of this algorithm in the presence of disturbances and noise was tested on several numerical examples. Lee et al. have also combined model predictive control with iterative learning control [12]. In doing so, the algorithm can accommodate both within-run and run-to-run errors. Srinivasan et al. proposed a constraint control scheme in the run-to-run framework to optimize the operation of a batch process and this approach is investigated in the present study for glucose control [22], [23], [24].

Insulin-dosing algorithms have been used in several commercially available products. For example, the Intelligent Dosing System (IDS™, Dimensional Dosing Systems, Wexford, Pa.) proposed by Cook et al. [25] has been used by clinicians to update the insulin therapy of patients on a month-to-month basis. The algorithm uses a nonlinear control law that relies on the glucose measurements (fasting or random glucose) and/or A1C values to determine the correct total daily dose of insulin. The insulin dose is determined such that the desired glucose measurement or A1C value is achieved at the next visit. This algorithm only makes recommendations to increase the total daily insulin dose; hence, the algorithm is one sided and does not address all aspects of the insulin therapy of the patient [26].

Another bolus dosing algorithm is the Bolus Wizard™ calculator (Medtronic Minimed, Northridge, Calif.), which allows the patient to set various blood glucose targets throughout the day [27]. The algorithm relies on blood glucose measurements, carbohydrate ratios, and insulin sensitivity factors to update the insulin therapy of a patient. The algorithm also accounts for the amount of active insulin in the body with the use of an insulin action curve.

However, existing insulin therapy schemes do not account for variations in meal composition, routines, physical activity and other influences on the insulin requirements of a patient. As a result, the insulin needs of the patient may still deviate from the levels predicted by regimen and present in the bloodstream, resulting in periodic episodes of hypoglycemia and hyperglycemia.

Accordingly, there is a need for a therapy for a patient with type 1 diabetes that permits the administration of insulin that mimics the physiologic needs of the patient and the normal insulin levels of a non-diabetic.

SUMMARY OF THE INVENTION

The present invention is a computer implemented method and associated apparatus, such as a microcontroller with programming implementing the method, for the combined control of insulin bolus dosing and basal delivery for the goal of achieving a normal glycemic response to meals, exercise, stressors, and other perturbations to blood glucose levels. The method, or control algorithm, comprises several elements or aspects of the invention, which can be used separately or beneficially in combination.

Another aspect of the invention is a run-to-run scheme that exploits the pattern of repeated postprandial glucose profile over a period of time to optimize the insulin bolus dose amount. A third aspect of the invention is a multi-model formulation in which different patient sensitivity models are employed, depending on the psychological, physical, hormonal stress levels (mild/moderate/severe) of the patient.

A further aspect of the invention is to provide a run-to-run control method of deriving both the optimal dosage of insulin to provide the basal insulin requirement (that dose of insulin that maintains normal blood glucose levels when there is no food ingested) and meal-related insulin dosing of an individual, comprising estimating a preprandial dosage of insulin for a subsequent day's corresponding meal based on the observed postprandial glucose response to the meal and preprandial dose of insulin for a current day.

Another aspect of the invention is to provide a method for predicting insulin need wherein a subsequent day's preprandial insulin dosages are corrected based on a previous day's meal-related postprandial glucose measurements incorporating the variables of time of day (to compensate for the diurnal variation of glucose tolerance), carbohydrate content of the meal, preprandial glucose concentration and time since last meal bolus.

Another aspect of the invention is a run-to-run control method of meal-related insulin dosing of an individual, comprising estimating a preprandial dosage of insulin for a subsequent day's corresponding meal based on observed response for a current day.

Another aspect of the invention is a predictive method of controlling blood glucose levels in a diabetic individual, comprising (a) measuring blood glucose level associated with a first time period; (b) as a function of said blood glucose level, estimating insulin bolus dosage associated with a second time period subsequent to said first time period; (c) administering said insulin bolus based on said estimate; and (d) repeating steps (a) through (c).

Another aspect of the invention is an apparatus for run-to-run control of meal-related insulin dosing of an individual, comprising a programmable computing device; and programming executable by said computer device for carrying out the operations of estimating a preprandial dosage of insulin for a subsequent day's corresponding meal based on observed response for a current day.

Another aspect of the invention is to provide an apparatus for control of plasma glucose levels that is robust and capable of accurately predicting insulin bolus dosages when a meal has been skipped or more than three meals are consumed in a day.

Another aspect of the invention is an apparatus for predictive control of blood glucose levels in a diabetic individual, comprising a programmable computing device; and programming executable by said computing device for carrying out the operations of (i) measuring blood glucose level associated with a first time period; (ii) as a function of said blood glucose level, estimating insulin bolus dosage associated with a second time period subsequent to said first time period; (iii) administering said insulin bolus based on said estimate; and (iv) repeating operations (i) through (iii).

Another aspect of the invention is that the estimated dosage for a subsequent time period can be higher than, lower than, or the same as, dosage for the current time period, the time periods preferably being current and subsequent days.

Another aspect of the invention is to normalize peak postprandial glucose levels following each meal.

Another aspect of the invention is to correct a subsequent day's preprandial insulin dosages based on previous days postprandial glucose measurements.

Another aspect of the invention is to repeat the estimating step or operation on a daily basis until dosages converge to a predetermined level.

Another aspect of the invention is to iteratively update the preprandial dosage of insulin for a subsequent day's meal over time. In one mode, the dosage comprises amount and timing.

Another aspect of the invention is to optimize adjustment of insulin dosing over time to achieve normal glycemic a response.

In one mode, a cycle comprises a twenty-four hour period during which breakfast, lunch and dinner meals are consumed.

In a second mode, a cycle comprises a twenty-four hour period during which fewer than or more than three meals are consumed by the patient.

In another mode, the estimating step or operation is a function of blood glucose level measurement and at least one parameter indicative of physical state of the individual. In one mode, the parameter indicative of physical state of the individual is selected from the group consisting essentially of the psychological, physical, hormonal stress levels (mild/moderate/severe) of the patient.

In another mode, the estimating step or operation is a function of blood glucose level measurement and meal size and timing.

In another mode, the estimating step or operation is a function of the blood glucose level measurement, meal size and timing, and at least one parameter indicative of physical state of the individual. In one mode, the parameter indicative of physical state of the individual is selected from the group consisting essentially of the psychological, physical, hormonal stress levels (mild/moderate/strenuous) of the patient.

In one mode, the first and second time periods, or current and subsequent days, are days during which at least one meal is eaten.

In another mode, the first and second time periods, or current and subsequent days, are twenty-four hour periods during which breakfast, lunch and dinner meals are eaten.

In another mode, the first and second time periods where fewer or more than three meals are eaten during the periods.

In another mode, the estimating step or operation determines amount and timing for meal-related bolus dosing for a subsequent day based on current day blood glucose level measurements.

The invention is beneficial in several respects, including the following:

(a) it combines the functions of both bolus and basal delivery;

(b) it improves glycemic control of both basal-related insulin requirement and meal-related insulin requirement (c) it allows patient customization through both the run-to-run component and the multi-model sensitivity element; and (d) it ensures robustness to intra- and inter-patient uncertainty.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only:

FIG. 6 is a plot of convergence of run-to-run algorithm within 10 days. The virtual patient is subject to a 20 g breakfast, 40 g lunch and 60 g dinner. The dotted lines represent the target boundaries of 90 and 140 mg/dl for $G^{min}$ and $G^{max}$, respectively. Top-Blood glucose concentration as a function of time: (dotted-dashed line) open-loop blood glucose concentration with no bolus, (solid line) blood glucose concentration on day 1 from initial guesses of insulin bolus amount and timing; (dashed line) blood glucose concentration on the second day using the run-to-run algorithm; (thick solid line) blood glucose concentration after 10 days of the run-to-run algorithm. Bottom: Corresponding insulin injection input for the run-to-run algorithm: (solid line) initial guess for insulin bolus injection; (dashed line) insulin bolus injection for day 2; (thick solid line) insulin bolus injection for day 10.

DETAILED DESCRIPTION OF THE INVENTION

Figure 1:
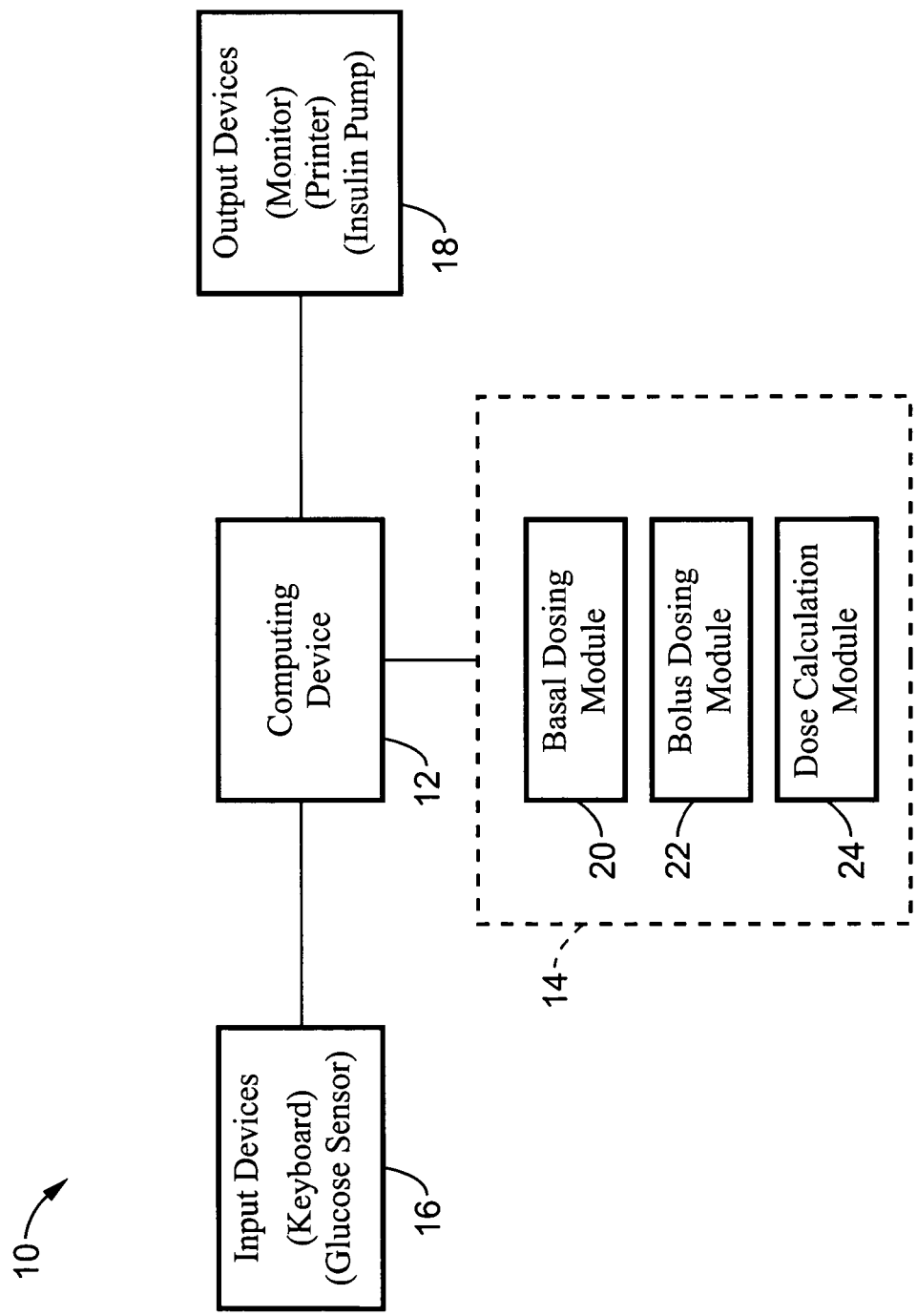
FIG. 1 is a schematic of one embodiment of an apparatus according to the present invention.

Referring more specifically to the drawings, for illustrative purposes the present invention is embodied in the apparatus generally shown in FIG. 1 through FIG. 16. It will be appreciated that the apparatus may vary as to configuration and as to details of the parts, and that the method may vary as to the specific steps and sequence, without departing from the basic concepts of the invention as disclosed herein.

The challenge of managing blood glucose concentrations through insulin injection is predicting the quantity of insulin that should be delivered and the frequency of insulin administration. Patients with type 1 diabetes may have two general types of doses to account for their insulin needs. The first is a "basal dose," which is a baseline amount of insulin that the body needs to function. The second is a "bolus dose" that is the amount of insulin needed to process digested sugars and carbohydrates due to the increased need for insulin after each meal. The term "dose" or "dosing" normally means the amount of insulin or insulin analog that is necessary to have the physiological effect of maintaining plasma glucose levels within the normal range. However, the term dose may also include a time of administration parameter. The present invention preferably provides a recommendation for the amount of insulin and the time of administration.

However, current treatments for diabetes by subcutaneous injection or continuous infusion often result in significant variations in the daily blood glucose concentration profile due to incorrect insulin dosing. Consequently, blood glucose levels may occur that may be above or below the target range for normal glycemia. Blood glucose levels outside of this preferred range prior to the next meal may create further insulin dosing inaccuracies with the use of conventional dosing schemes.

Three meals are usually consumed in the normal day, each having a different quantity, caloric content and carbohydrate composition. Therefore, the timing and quantity of insulin that is used needs to be adapted to the nature of the food ingested and account for the temporal insulin status of the patient. One important objective of the invention is to provide meal-to-meal control over blood glucose concentrations so that they are maintained within a preset minimum and maximum glucose concentration with the use of a run-to-run control scheme. The control algorithm exploits the repetitive nature of the insulin therapy regimen of a diabetic patient.

The repetitive nature of an intensive glucose control therapy regimen (i.e., taking blood glucose measurements, eating meals, and delivering the correct bolus of insulin) is analogous in some ways to industrial batch processes, such as seen in semiconductor manufacturing. On a day-to-day basis, the patient is performing the same tasks to adjust their insulin therapy in order to maintain blood glucose concentrations within appropriate boundaries.

In the preferred embodiment of the present invention, each meal is considered to be a run. Measurements from one or more previous runs are used to adjust the manipulated variables in the present run in order to push the system toward pre-selected endpoints. Thus, measurements from the previous meal cycles may be used to correct the insulin bolus amount and timing for the current cycle. Because the measurements are taken at the end of each run, the algorithm should be responsive to transitory influences on the insulin needs between runs and cycles. Furthermore, even though the parameters vary from patient to patient, the algorithm iteratively determines the insulin injection profile without knowing the starting parameters of the patient. Feedback allows refinement of the parameters and specific dosing over successive cycles.

Accordingly, an apparatus and method for controlling the blood glucose level of a patient with Type 1 diabetes is provided that uses measurements from previous meal cycles to iteratively determine the future insulin injection therapy for the patient. The daily cycle of the patient with diabetes is treated as a batch (run-to-run) process. For a person with diabetes, each day represents a single run. From the blood glucose measurements obtained at the end of the day, the insulin therapy can be adjusted for the next day. Hence, the run-to-run algorithm aims to employ readily available data to improve the insulin therapy of the patient.

Turning now to FIG. 1, a schematic of one embodiment of an apparatus 10 of the invention is generally shown. In this embodiment, the apparatus 10 generally comprises a computing device 12 that has programming 14 configured to interface with any number of input devices 16 and output devices 18. The programming 14 has a basal dosing module 20, a bolus dosing module 22 and a dose calculation module 24 in the embodiment shown in FIG. 1. The computing device preferably has suitable memory to store programming and data and provide access to the data.

The computing device 12 is operably coupled with any number of input devices 16 that provide relevant data, command functions and other input to the computing device. One of the input devices 16 is preferably a keyboard or a keypad. The input device 16 may also be a second computing device such as a personal or laptop computer. The keypad or other input device 16 may be coupled to the computing device 12 through a wired coupling or may be coupled by wireless connections such as radio frequency or infrared.

The keypad or similar input device 16 is used to provide glucose measurements and other relevant data and information to the programming 14. Throughout the course of the day, the glucose profile of a patient may change rapidly and frequent glucose monitoring is necessary to illustrate trends and provide an accurate profile. Devices for the invasive and non-invasive measurement of blood glucose levels are presently available. Invasive monitoring requiring an extracted sample of blood to quantify blood glucose is often annoying and painful to the patient and has a natural limit to the number of samples in a given time period that the patient can tolerate. The present invention may reduce the number of samples necessary to properly monitor the blood glucose level of the patient.

Non-invasive sensing devices can yield sparse, semi-continuous or continuous blood glucose measurements. In another embodiment, one of the input devices 16 comprises a blood glucose sensor that is configured to automatically sample and report glucose levels to the computing device 12 at regular intervals. Fully implantable continuous glucose sensors are capable of frequent sampling and blood glucose or other measurements. Other glucose concentration sensors may also be used including semi-invasive sensors that minimally breach the outer skin layers, continuous sensors that measure glucose at an essentially constant or rapid manner and non-invasive sensors that measure glucose levels without breaking the skin. Accordingly, spot measurement meters, continuous glucose measurement devices, near infrared based sensors, spectroscopy based sensors, fluorescence based sensor and the like may be used.

The information and data provided by the keypad or other input device 16 permits the programming 14 to provide a bolus and basal dosing to the patient through one or more output devices 18. The output devices 18 may provide a variety of outputs to display, provide information, store information, and transmit information, or to actuate an insulin pump etc. For example, the output device 18 coupled to the computing device 12 may be a monitor or display to depict processed data and the recommendation for insulin dosing. The computing device 12 may also control an output device 18 that is a printer or plotter to depict processed information graphically. In another embodiment, the output device 18 is an insulin pump that is configured to be controlled directly by the computing device 12 or indirectly through a suitable input device 16. In this embodiment, the computing device is sized to permit implantation in a patient and is operably coupled to an insulin pump to provide insulin doses at any time to the patient during a cycle. Instructions and data may be transmitted to the implanted computing device 12 or to an insulin pump by radio frequency in this embodiment. The output device 18 may also be a communication device to permit wireless communications with other devices.

It can be seen that the computing device 12 can be configured in many forms. The apparatus may be a full sized computer or be adapted to be a hand held device, a watch style device that is strapped to the arm of the user or sized to be implanted in the patient. In another embodiment, the computing device 12 may also be configured to be in communication with a network operated by a physician or care provider through a closed network or through Internet access to permit the transfer of data and provide general oversight of the patient's condition by their physician. Other computing devices such as a laptop, PDA or other device that has a distributed computing environment with computations conducted on a remote server, messaging system, telephony system, cell phones, or other device capable executing an algorithm or hardware programmed that can keep track of time based events may be used.

Basal dosing module 20 of programming 14, preferably provides programming that will optimize the basal insulin dosing using sparse measurements and run-to-run control algorithms. Insulin pumps are particularly effective in providing a large number of small quantity doses to maintain a basal insulin concentration without driving the plasma glucose levels down between meals or during sleep. However, a basal dose may also be administered orally or by injection when separate basal dosing is required and is not limited to insulin pumps. Other means for delivering insulin include patches, nasal or inhalers, oral, intravenous and other peritoneal implantable delivery systems can be used.

Figure 2:
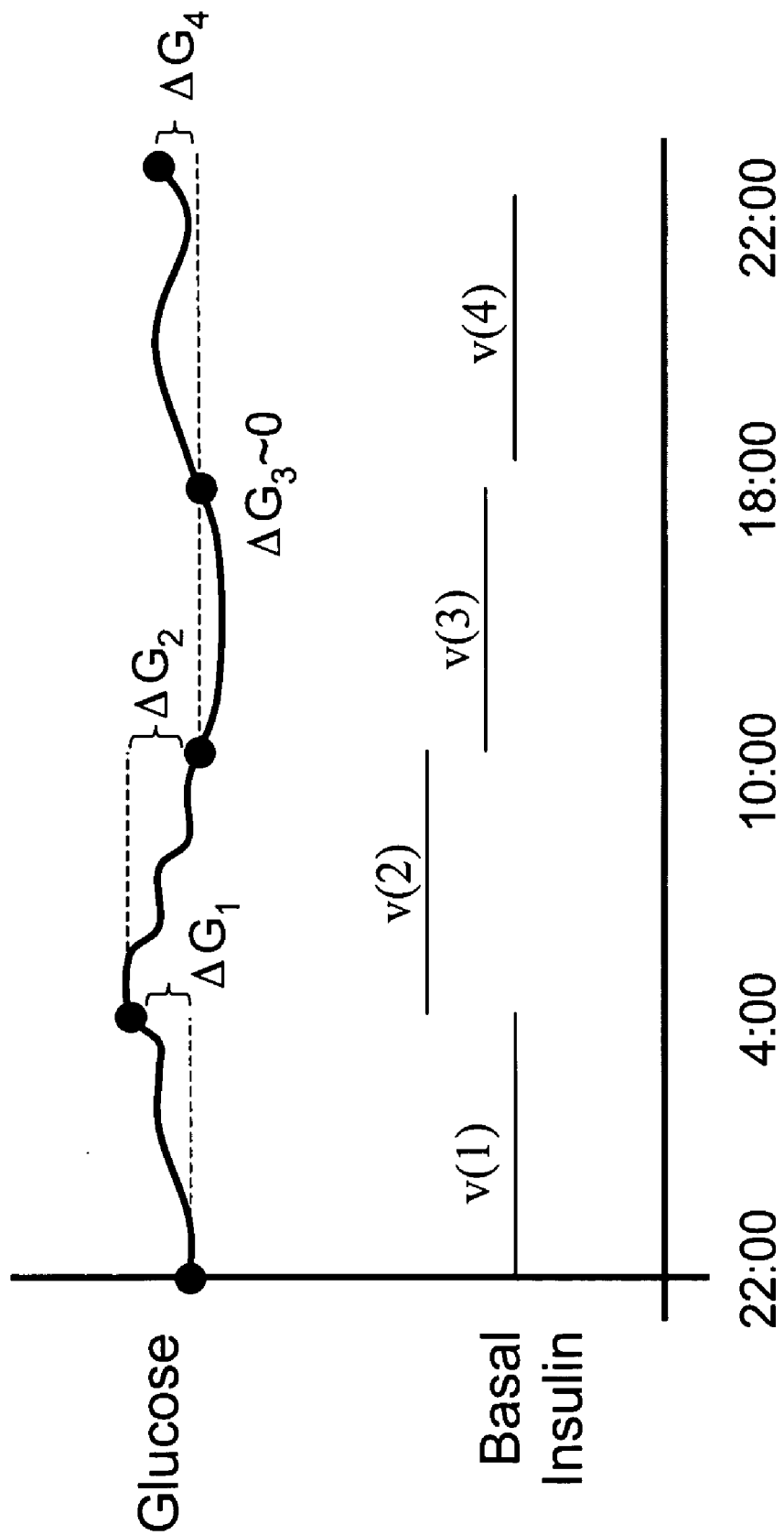
FIG. 2 is a plot of basal insulin and glucose levels over four time segments where $v_k$ equals the magnitude of each basal insulin segment for batch k and $\psi_k$ is the magnitude of the glucose deviation across segment for batch k.

One method for adjusting or recommending basal infusion rates using sparse measurements it through the use of run-to-run control in the basal dosing module 20 of FIG. 1. In an illustrative embodiment, a 24-hour day can be divided into segments during which the basal insulin infusion rate may be adjusted independent of the others as shown in FIG. 2. Such adjustments accommodate the changing insulin requirements due to the sleep-awake cycle and changing levels of activity during the day. Although the number of segments and the corresponding timing can be selected on a patient-by-patient basis, the control algorithm is preferably described using the standard first-choice of four segments comprising: a) midnight to 4 am, b) 4 am to 10 am, c) 10 am to 6 pm and d) 6 pm to midnight.

In the absence of meals or other events affecting blood glucose levels (e.g. exercise), the basal insulin infusion rate must keep the patient's blood glucose in the normal range of 70-100 mg/dl. If the amount of insulin infused ("basal dose") over the time segment is too low, the blood glucose level will rise above the desired range; if the basal dose is too large, it will tend to lower blood glucose into the hypoglycemic range. Either of these circumstances requires that the amount of insulin infused be adjusted accordingly. Using the run-to-run strategy, preferably each day is considered a "cycle." Thus, for the current day a performance measure is calculated for each segment and that measurement is then used to adjust the amount of insulin for each corresponding segment on the following day. In another embodiment, each day is considered to be a run and the cycle being several days or a week.

For example, in the case when there are no meals or other events during the segment in question, a blood glucose measurement can be taken at the start and end of the segment. Regardless of the blood glucose level coming into the segment, the perfect basal insulin amount during the segment should keep this level constant. Thus a deviation ($\Delta G = G_{end\,of\,segment} - G_{start\,of\,segment}$) is a performance measure that can be used as the controlled variable.

When a meal or exercise is present, a blood glucose sample at an earlier or later time can be substituted. For example, for a segment covering 4 am to 10 am and breakfast is consumed at 8 am, the blood glucose measurements at 4 am and 8 am can be used, thus avoiding the confounding influence of the meal if a measurement at 10 am were used. Similarly, a measurement later can be used in the segment if there is an event shortly before the start of the segment.

Accordingly, the controlled variable vector can be constructed as:

$$\psi^T = [\Delta G_1 \Delta G_2 \Delta G_3 \Delta G_4]$$

The preferred run-to-run control algorithm for basal dosing is given below:

1. Parameterize the input profile for run k, $u_k(t)$ as $U(t, v_k)$. Also, consider a sampled version, $\psi_k$ of the output, $y_k(t)$, such that the input parameter vector, $v_k$, and the controlled variable vector $\psi_k$ have the same dimension. This gives the equation:

$$\psi_k = F(v_k)$$

2. Choose an initial guess for $v_k$, k=1.
3. Complete the run using the input $u_k(t)$ corresponding to $v_k$. Determine $\psi_k$ from the measurements $y_k(t)$.
4. Update the input parameters using, $$v_{k+1} = v_k + K(\psi^r - \psi_k)$$

where K is an appropriate gain matrix and $\psi^r$ represents the reference values to be attained. Set k:=k+1 and repeat steps 3-4 until convergence.

The recommendation of the basal module 20 can also be adjusted in the dose calculation module 24 in the embodiment shown in FIG. 1 to account for physiological conditions that increase or decrease the basal insulin needs. The psychological, physical, hormonal stress levels (mild/moderate/severe) as well as the exercise level (mild, moderate or strenuous) of the patient can also influence basal dose insulin requirements.

In one embodiment, the patient can indicate their state to the algorithm, which can then use the appropriate model for the selected state. The data accumulated for each run in a given condition is clustered accordingly. For example, a patient could have a standard day, followed by two days of moderate psychological stress, and then back to normal. The adjustments during the moderate psychological stress days would be based on the calculations of the previous day (which could be as many as several days before). Similarly, the adjustments made by the algorithm during these two days of stress would not carry over into the normal day, but the algorithm would go back three days back to the last normal day instead.

Accordingly, the basal insulin needs and dosing can be optimized alone or in conjunction with optimization of bolus Insulin dosing. This basal optimization can also account for conditions that result in variable insulin needs such as illness or exercise.

Referring still to FIG. 1, the programming 14 also includes a bolus dosing module 22 that provides bolus dosing recommendations in the embodiment shown. The bolus dosing module 22 preferably provides programming that will optimize the bolus dosing requirements of diabetic patient using a run-to-run (R2R) control algorithm. It can be seen that the apparatus shown in FIG. 1, can provide both an episodic basal dose and bolus dose recommendations as well as be configured to provide continuous recommendations to various insulin pump configurations to provide insulin dosing on a continuous basis.

Figure 3:
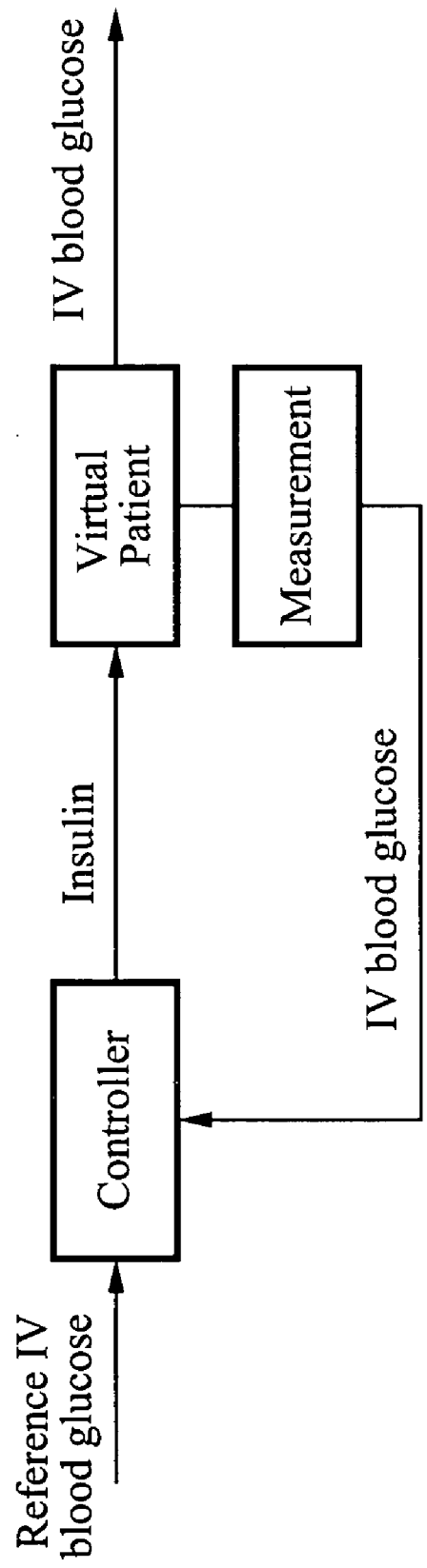
FIG. 3 is a schematic of the closed-loop system for computer studies of direct control of IV blood glucose. The measurement device sends the glucose readings to the controller to optimize the insulin dose at the next sample time.

The schematic representation in FIG. 3 of a closed loop system for control of plasma glucose levels also can be used for basal and bolus dosing calculations. The schematic shows a controller, a measurement device and a virtual patient model to provide a bolus dose recommendation. The controller preferably uses a run-to-run control algorithm using plasma glucose measurements and a virtual patient model that is configured to account for various influences on the insulin needs from exercise, fitness, illness and psychological, physical and hormonal stress.

Patient Model

For the purposes of this invention, the Bergman model is employed (the results with the Sorensen and AIDA model are also provided and the results are highlighted in Table 3). With the Bergman virtual patient it is feasible to simulate a 24-hour day of meal intakes (breakfast, lunch and dinner) and the corresponding meal related bolus doses for the diabetic patient.

The term "meal" used herein shall mean a discrete carbohydrate intake event which may include a meal in the traditional sense of the word and may also include large snacks or intake of food or drink that results in a substantial increase in plasma glucose levels. It is preferred that the carbohydrate intake events be separated by time periods of more than approximately two hours. The size, composition, duration, timing and number of intake events are also relevant to the definition of a meal. Meal duration can be further divided into meal eating periods and meal absorption periods, which may overlap.

For each meal, the desired measurements are the maximum glucose concentration, $G^{max}$, and the minimum glucose concentration, $G^{min}$. Each meal requires the appropriate insulin bolus to mediate rising blood glucose concentrations. Therefore, the timing, T, and the amount, Q, of the insulin dose must be adjusted to yield the desired $G^{max}$ and $G^{min}$ value for each meal.

The generally accepted normal range of glucose levels is a preprandial (or fasting) blood glucose concentration of 70 to 100 mg/dl, and a postprandial peak blood glucose concentration of 110 to 150 mg/dl. Although the present invention has the capacity to target narrower ranges down to a preprandial and postprandial glucose concentration differential of no more than 10 mg/dl above the lower level of normal. Accordingly, the invention can be adapted to include narrower ranges in the event that the generally accepted normal range is further reduced.

For clinical application of the run-to-run algorithm, $G^{max}$ and $G^{min}$ may be translated into appropriate markers for quality of glucose regulation that occur at fixed time points (to limit measurement requirements). For example, with insulin aspart, the maximum insulin concentration occurs approximately 60 minutes after the insulin bolus. The 60 minute blood glucose concentration, $G^{60}$, occurs 60 minutes after the start of a meal, and the 90 minute blood glucose concentration, $G^{90}$, is lower than $G^{60}$. These time points will depend upon both the peak effectiveness and the elimination dynamics of the insulin used. Although the 60 and 90 minute time periods are preferred, it will be understood that other time periods as well as other derivative functions can be applied to the data without departing from the invention.

Run-to-Run Control Algorithm

The preferred run-to-run control algorithm for bolus dosing is given below:

1. Parameterize the input profile for run k, $u_k(t)$ as $U(t, v_k)$. Also, consider a sampled version, $\psi_k$, of the output, $y_k(t)$, such that the input parameter vector, $v_k$, and the controlled variable vector $\psi_k$ have the same dimension. This gives the equation:

$$\psi_k = F(v_k)$$

2. Choose an initial guess for $v_k$, $k=1$.
3. Complete the run using the input $u_k(t)$ corresponding to $v_k$. Determine $\psi_k$ from the measurements $y_k(t)$.
4. Update the input parameters using, $$v_{k+1} = v_k + K(\psi^r - \psi_k)$$

where K is an appropriate gain matrix and $\psi^r$ represents the reference values to be attained. Set $k:=k+1$ and repeat steps 3-4 until convergence.

The convergence of the run-to-run algorithm can be determined by analyzing the dynamics of the error for the closed-loop system, where the error is shown by $e_k = (\psi^r - \psi_k)$.

For this analysis, the equation $\psi_k = S v_k$ is used which is a linearized version of the system equation $\psi_k = F(v_k)$ where $$S = \frac{\partial F}{\partial v}$$

is the sensitivity matrix.

The linearized error dynamics are easily derived through the following manipulations of the preceding equations:

$$v_{k+1} = v_k + K(\psi^r - \psi_k)$$

$$S v_{k+1} = S v_k + SK(\psi^r - \psi_k)$$

$$\psi^r - S v_{k+1} = \psi^r - (S v_k + SK(\psi^r - \psi_k))$$

$$\psi^r - \psi_{k+1} = \psi^r - \psi_k - SK(\psi^r - \psi_k)$$

$$e_{k+1} = e_k - SKe_k = (I - SK)e_k$$

Hence, the eigenvalues of the matrix (I–SK) should be within the unit circle for the algorithm to converge. Also, note that convergence of the algorithm is determined by the controller gains K and the sensitivity matrix S.

The application of run-to-run control to help manage diabetes provides an opportunity to properly adjust the current insulin therapy of the patient. The run-to-run algorithm exploits the repetitive nature of the insulin therapy regimen of the diabetic patient. For each meal, an update law is provided to correct the insulin bolus amount and timing for the next day. For the present application, $u_k(t)$ and $y_k(t)$ correspond to the insulin and glucose profiles, respectively, where t is the continuous time variable and k the run number. The run index k represents the repetition of the 24-hour daily routine of breakfast, lunch and dinner meals.

Definition of Variables

Three different meals are considered over a 24-hour period as the basic cycle, which is repeated.

Manipulated variables: Timing of three insulin injections for breakfast, $T_B$, lunch, $T_L$, and dinner, $T_D$, and quantity of insulin injection for breakfast, $Q_B$, lunch, $Q_L$, and dinner, $Q_D$, to provide: $v^T = [T_B Q_B T_L Q_L T_D Q_D]$ Controlled variables: Maximum value of glucose attained after breakfast, $G_B^{max}$, lunch, $G_L^{max}$, and dinner, $G_D^{max}$, and the minimum value of glucose attained after the peaking for breakfast, $G_B^{min}$, lunch, $G_L^{min}$, and dinner, $G_D^{min}$ to provide:

$$\psi^T = [G_B^{max} G_B^{min} G_L^{max} G_L^{min} G_D^{max} G_D^{min}]$$

The maximum and minimum glucose concentrations are selected as convenient scalar measures of performance for a particular insulin regime. As before, pragmatic considerations may dictate that time points are used to approximate maximum and minimum values.

The insulin sensitivity matrix of the person with diabetes, S, is characterized to aid in the selection of the controller gain matrix. Here, the patient sensitivity reflects the breadth of output variable responses, $\psi$ as a function of changes in the input variable, v. This does not characterize the insulin sensitivity of the virtual patient in the traditional sense, as the transient glucose profile is not analyzed completely, only the desired output variables.

S is composed of the sensitivity values for breakfast, lunch and dinner. The elements of the matrix $s_{i,j}$ represent the sensitivity of the $j^{th}$ output in response to variations in the $i^{th}$ input. For example, $s_{1,1}$ denotes the change in the maximum glucose concentration for breakfast $G_B^{max}$ to a unit change in the timing of the breakfast bolus $T_B$. Accordingly, $s_{3,1}$ corresponds to a non-causal relationship between the timing of the lunch bolus $T_L$ and $G_B^{max}$ and thus is zero. The patient sensitivity may be determined, separately, using a local estimation, and a global estimation technique.

Local Estimation of Patient Sensitivity

The local insulin sensitivity of the virtual patient, which corresponds to approximating the derivative $$\frac{\partial F}{\partial v}$$

around the current operating point, was computed numerically using a finite difference approximation. The timing of the bolus was varied ±5 minutes from nominal and the amount of the bolus was varied approximately ±5 to 10% of the nominal for all three meals. The operating point used was $G^{max*} = 140$ mg/dl, $T_B^* = 155$ min, and $Q_B^* = 2.2e6$ µU/ml. The units result from the normalization by volume by the Bergman model. The profile of the local estimation of the insulin sensitivity can be observed by the light gray plane in FIG. 4.

Global Estimation of Patient Sensitivity

Figure 4:
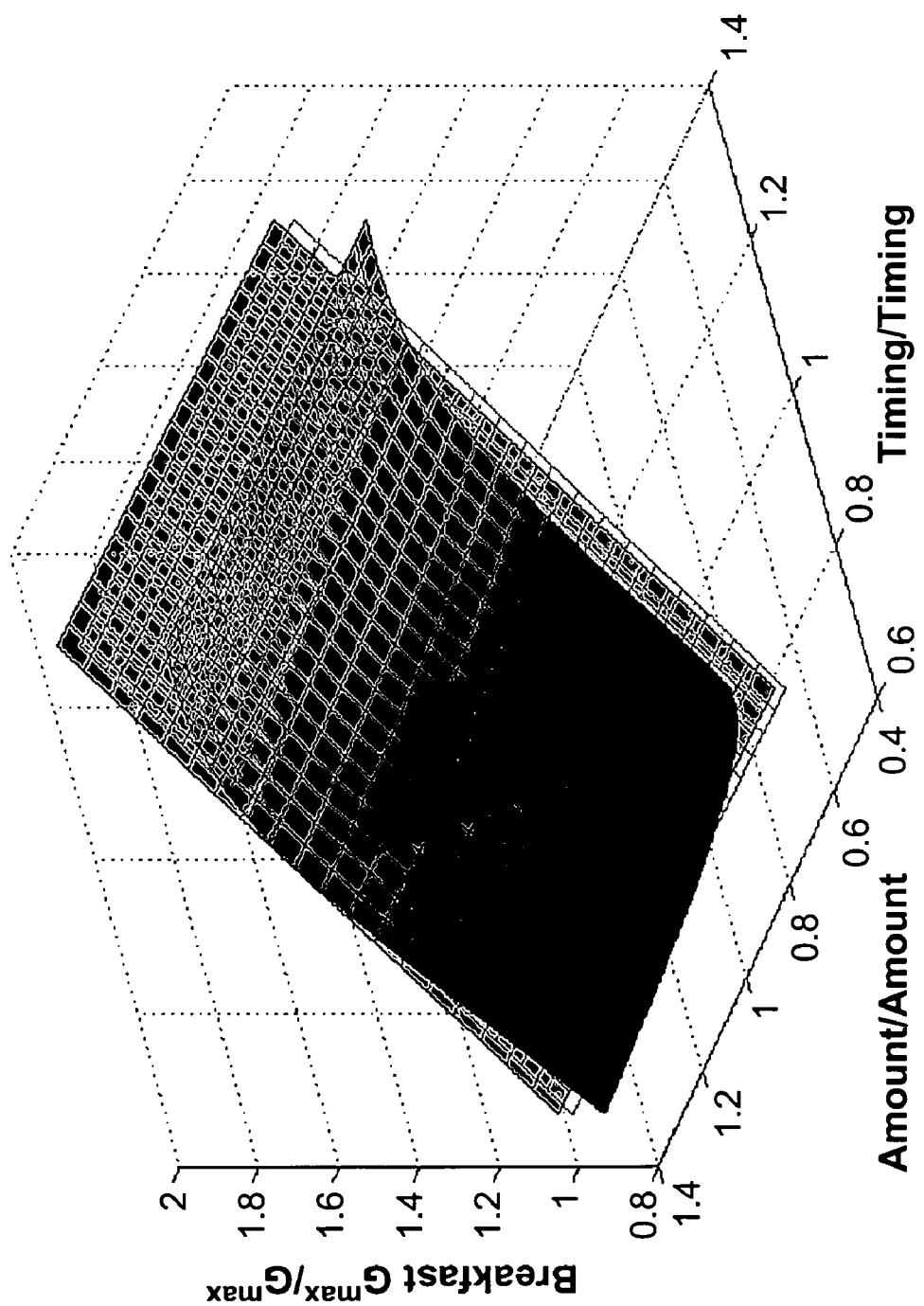
FIG. 4 is a plot of maximum glucose concentration $G^{max}$ for the breakfast meal as a function of the insulin amount and the insulin timing. $G^{max*}=140$ mg/dl, Timing*=155 min, and Amount*=2:2e6 µU/ml. The units result from the normalization by volume by the Bergman model. The dark solid curve represents $G^{max}$ as calculated from the nonlinear model. The light grey plane represents the dynamics of $G^{max}$ from a local estimation of the insulin sensitivity of the patient. The clear plane represents the dynamics of $G^{max}$ from a global estimation of the insulin sensitivity of the patient.

FIG. 4 also shows the maximum blood glucose concentration for the breakfast meal as a function of the insulin dose amount and insulin dose timing covering a wider range (±40%). The dark curved surface represents the actual response of the virtual patient model. As the amount of the bolus increases, the $G^{max}$ decreases slightly, and as the timing of the bolus moves forward well beyond its impact on the breakfast meal, $G^{max}$, begins to increase asymptotically up to the open-loop $G^{max}$ concentration. This is done for all three meals and all six output variables. As the timing of the insulin bolus moves past the peak, the $G^{max}$ concentration for breakfast increases.

These nonlinearities necessitate a global estimation of the patient sensitivity, which was determined by varying the timing of the insulin bolus and the amount over a wider range (±40%). Three sets of sample points were generated corresponding to the three meals. Each set had points from a 2-dimensional grid (18×18) where the axes were the insulin bolus quantity and timing of injection corresponding to the meal considered. Thus, the number of points generated was N=3×18×18=972. After obtaining the surface, a least-squares fit may be performed using the MATLAB fmincon routine with the cost function given below to determine the corresponding best-fit sensitivity:

$$\min_{S} \sum_{i=1}^{N} \|\psi_i - Sv_i\|^2$$

The fit from the global determination of the insulin sensitivity is given by the clear plane in FIG. 4. Similar to the response of the nonlinear model, $G^{max}$ increases as the bolus timing moves away from the meal peak.

Controller Design

In principle, a multivariable controller should be designed to maintain the components of $\overline{A}$ at their reference values $\psi^r$. However, the sensitivity matrix shows that the effects of the inputs are relatively decoupled for the case studies considered (as determined by the relative gain array (RGA)). The RGA for the Bergman model subject to breakfast (20 g, 8 A.M.), lunch (40 g, 12 noon) and dinner (60 g, 5 P.M.) is calculated below):

$$RGA = \begin{bmatrix} 1.0068 & -0.0068 & 0.0 & 0.0 & 0.0 & 0.0 \\ -0.0068 & 1.0068 & 0.0 & 0.0 & 0.0 & 0.0 \\ 0.0 & 0.0 & 0.9306 & 0.0694 & 0.0 & 0.0 \\ 0.0 & 0.0 & 0.0694 & 0.9306 & 0.0 & 0.0 \\ 0.0 & 0.0 & 0.0 & 0.0 & 0.9519 & 0.0481 \\ 0.0 & 0.0 & 0.0 & 0.0 & 0.0481 & 0.9519 \end{bmatrix}$$

First of all, the RGA suggests that there is no coupling between the meals. For each meal, there are two outputs ($G^{min}$ and $G^{max}$) and two inputs (T and Q). Again, the RGA suggests pairing, for each meal, the timing T of the insulin bolus with the maximum glucose concentration $G^{max}$ and the quantity Q of the insulin bolus with the minimum glucose concentration $G^{min}$. The appropriate controller gain matrix K corresponds to a diagonal matrix as given below:

$$K = \begin{bmatrix} k_{T_B} & 0 & 0 & 0 & 0 & 0 \\ 0 & k_{Q_B} & 0 & 0 & 0 & 0 \\ 0 & 0 & k_{T_L} & 0 & 0 & 0 \\ 0 & 0 & 0 & k_{Q_L} & 0 & 0 \\ 0 & 0 & 0 & 0 & k_{T_D} & 0 \\ 0 & 0 & 0 & 0 & 0 & k_{Q_D} \end{bmatrix}$$

where $k_T$ is the controller gain for the timing control loop of the meal (breakfast (B), lunch (L) and dinner (D)) and $k_Q$ the controller gain for the corresponding quantity control loop.

The important variables that need to be designed are the initial guesses $v_1$. In addition to $G^{max,r}$ and $G^{min,r}$ (desirable bounds on glucose), there exist the hard limits $\overline{G}^{max}$ and $\overline{G}^{min}$ (absolute bounds that, if violated, can lead to serious medical problems). The $v_1$ should be chosen such that these hard constraints are satisfied for all cases. Also, the history of the patient can facilitate the selection of initial guesses.

For all three meals, the desired reference value for $G^{max}$ was set to 140 mg/dl and the target for $G^{min}$ to 90 mg/dl. The controller gains $k_T$ and $k_Q$ were computed in accordance to the insulin sensitivity of the virtual patient. Though the coupling is low, it might so happen that a fast decrease in $G^{max}$ may cause an unacceptable response in $G^{min}$ and vice versa. Thus, the gains reflect a compromise between speed and accuracy.

The limited measurement information regarding the blood glucose level of the patient is translated into quality measurements (max/min glucose). Accordingly, it can be seen that the sampling protocol of the patient does not need to be rigorously synchronized to a particular time every day.

A very strong decoupling between manipulated and controlled variables is observed. In addition, it is also observed that the morning meal and associated insulin injection has a negligible influence on the measured glucose concentrations after lunch or dinner.

It can be seen that the "optimal" maximum glucose value or range is achieved after several meal cycles while the "optimal" minimum glucose values are established rather quickly.

Another major influence on the quantity of insulin needed by the body is the degree of stress. Stress comes in three forms and the insulin response is proportional to the degree of stress in each case whether it is psychological, physical or hormonal stress. Mild, moderate or severe psychological stress changes the normal quantity of insulin that is needed to maintain blood glucose levels within proper limits. Likewise, physical stress from illness such as inflammatory responses, infections or traumatic injury as well as hormonal variations, such as puberty, menses, pregnancy or menopause can substantially change the insulin needs of an individual. Because the body responds to stress by increasing the normal basal and meal-related insulin-secretory response, the daily insulin dose must be increased to compensate for the stress in the diabetic patient. New or existing models can be used that account for the increased insulin need due to stress or illness as well as other influences that are discovered in the future. In addition, exercise decreases the insulin requirement. The decrement in insulin requirement is proportional to the degree of energy expenditure and thus is related to the degree of exercise: mild moderate or strenuous exercise. New or existing models can be used to incorporate the decrease in insulin requirement due to exercise in addition to the increased needs in the cases of associated stress.

Thus, the dose calculation module 24 and the bolus dosing module can provide an insulin dosage recommendation that accounts for the activity, fitness and stress and other known effects on the insulin needs of the patient and maintain plasma glucose levels within a desired range.

The present invention may be more particularly described in the following examples that are intended for illustrative purposes only, since numerous modifications, adaptations and variations to the apparatus and methods will be apparent to those skilled in the art.

EXAMPLE 1

To accurately simulate the meal-to-meal control of blood glucose concentration through insulin therapy of patients with Type 1 diabetes, a run-to-run algorithm is used on a virtual diabetic patient model to control blood glucose concentrations. The algorithm of the present invention can be adapted for evaluation with any number of virtual patient models for diabetes that presently exist. The following example emphasizes results evaluated in the Bergman model. However, the algorithm was also used with the Sorensen and Automated Insulin Dosage Advisor (AIDA) design virtual patient systems for comparison and to confirm the results.

The Bergman model is a three compartment minimal model of glucose and insulin dynamics. This 3rd-order model is comprised of a glucose compartment, (G), a remote insulin compartment, (X), and an insulin compartment, (I). The remote insulin compartment mediates glucose uptake within the glucose space to the peripheral and hepatic tissues. The insulin distribution space combines the sinks and sources of insulin production and consumption into a single pool. While simplistic in nature, the Bergman model is able to capture certain dynamics of the diabetic patient system.

The Bergman virtual patient model simulates a 24-hour day of meal intakes (breakfast, lunch and dinner) and the corresponding meal related bolus doses for the diabetic patient. For each meal, the desired measurements are the maximum glucose concentration, $G^{max}$, and the minimum glucose concentration, $G^{min}$. Each meal requires the appropriate insulin bolus to mediate rising blood glucose concentrations. Therefore, the timing, T, and the amount, Q, of the insulin dose must be adjusted to yield the desired $G^{max}$ and $G^{min}$ value for each meal.

To demonstrate the ability of the run-to-run control algorithm to regulate blood glucose concentrations, the virtual patient model is subject to a 20 g breakfast, 40 g lunch and 60 g dinner, with an initial guess for the insulin regimen. The meal times were fixed at 8 am, 12 noon and 5 pm. Generally, the insulin input is parameterized into the timing and amount of the dose while the glucose output is parameterized into the maximum and minimum glucose concentrations. By parameterizing the insulin input (Q and T) and the glucose output ($G^{max}$ and $G^{min}$) for breakfast, lunch and dinner, appropriate control laws were derived. To tune the controller, the insulin sensitivity of the virtual patient was determined by examining the $G^{max}$ and $G^{min}$ as a function of the timing and amount of the insulin dose.

For each meal, an update law is prescribed to correct the insulin bolus amount and timing for the next day. For the present application, $u_k(t)$ and $y_k(t)$ correspond to the insulin and glucose profiles, respectively, where (t) is the continuous time variable and (k) the run number. The run index (k) represents the repetition of the 24-hour daily routine of breakfast, lunch and dinner meals.

The desired reference value for $G^{max}$ for all three meals was set to 140 mg/dl and the target for $G^{min}$ to 90 mg/dl. The controller gains $k_T$ and $k_Q$ were computed in accordance to the insulin sensitivity of the virtual patient. Though the coupling is low, it might so happen that a fast decrease in $G^{max}$ may cause an unacceptable response in $G^{min}$ and vice versa. Thus, the gains reflect a compromise between speed and accuracy.

Figure 5A:
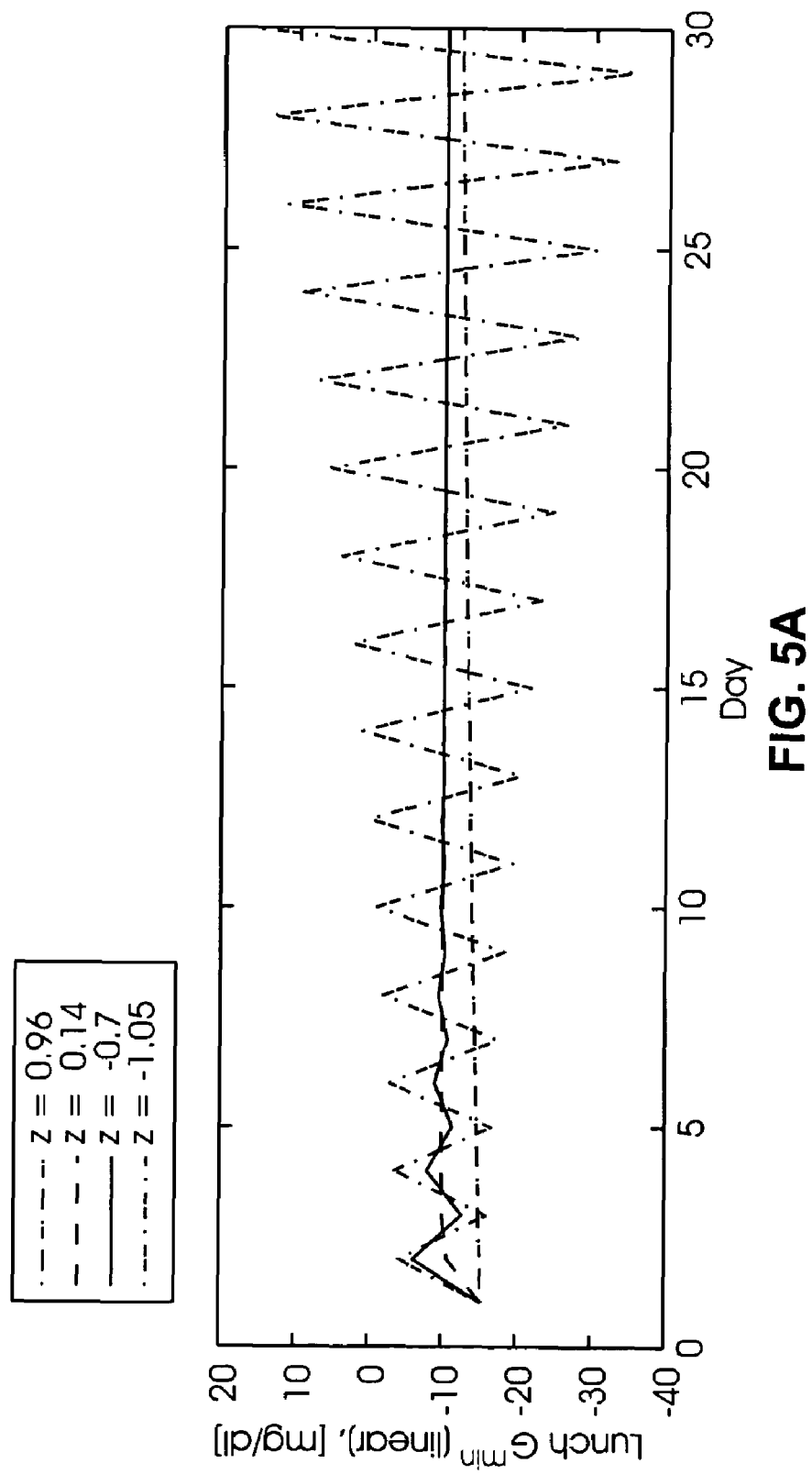
FIG. 5 is a plot of $G^{min}$ for the lunch meal as a function of the pole location. Top-Convergence speed of linear Bergman model as the pole moves along the real axis: (dashed-dotted line) slow convergence, z=0.96; (dashed line) fast convergence, z=0.14; (solid line) fast convergence with oscillations, z=−0.7; (dotted line) diverging with oscillations, z=−1.05. Bottom-Corresponding convergence speed of the nonlinear Bergman model. As the controller gain is increased, the virtual patient model eventually diverges, as shown from the dotted line.

The graph of FIG. 5A is a plot of $G^{min}$ for the lunch meal as a function of the pole location and shows the convergence of the run-to-run control algorithm for the lunch meal of the Bergman model. Specifically, the convergence speed of linear Bergman model as the pole moves along the real axis is shown for slow convergence z=+0.96 (dashed-dotted line) and z=+0.14 (dashed line), as well as fast convergence with oscillations, z=−0.7; (solid line) and diverging with oscillations, z=−1.05 (dotted line). The convergence properties of $G^{min}$ for lunch are shown for the linear model in FIG. 5A, employing the patient sensitivity, and the full nonlinear model shown in corresponding FIG. 5B.

Figure 5B:
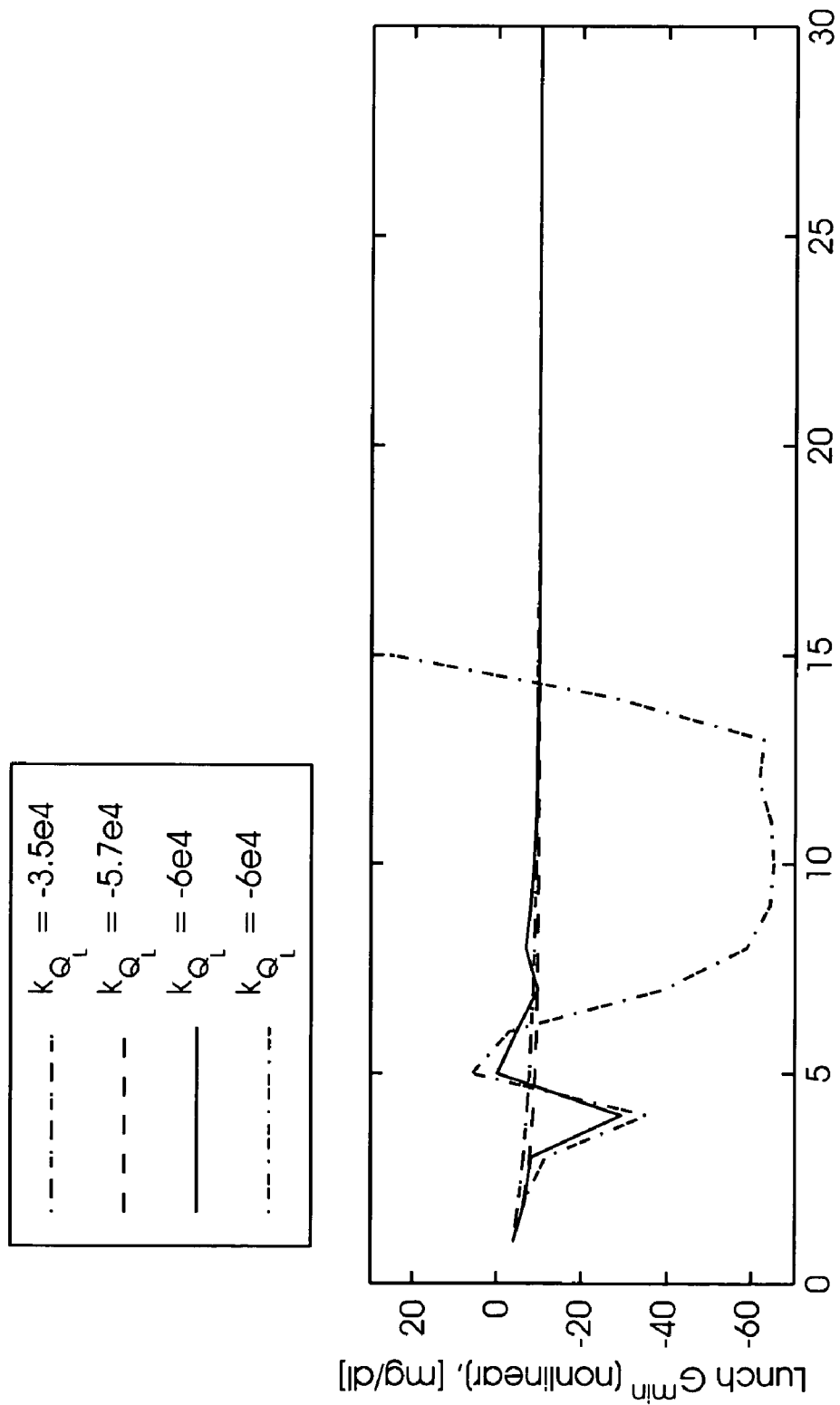

As can be seen from the plot in FIG. 5A, the linear model quickly converges when the poles lie within the unit circle. As these poles move away from the origin in the left half plane, convergent oscillations develop and eventually, the system diverges as the poles lie outside the region of stability denoted by the unit circle. The plot of FIG. 5B shows the response of the nonlinear model as the control loop is tuned. As the controller tuning becomes more aggressive, the system begins to oscillate and eventually diverges.

Table 1 lists the patient sensitivity values for the Bergman model employed to evaluate the error dynamics of the system and determined from the global estimation of the insulin sensitivity of the virtual patient model. The corresponding controller gains are given in Table 2. The control loops were tuned to converge as quickly as possible with minimum oscillation in the virtual patient model response. In Table 2, the differences in the controller gains reflect the nonlinearity and the interactions within the system. All of the subsequent results are based on these controller tunings.

Turning now to FIG. 6A and FIG. 6B, a plot of convergence of run-to-run algorithm over a ten day period and the corresponding insulin injection times and quantities are shown. The virtual patient is subjected to a 20 g breakfast, 40 g lunch and 60 g dinner. FIG. 6A demonstrates the ability of the run-to-run algorithm to control blood glucose concentrations and converge to the desired preprandial goal of between 90 mg/dl and postprandial goal of 140 mg/dl for $G^{max}$ and $G^{min}$ (shown by the horizontal dotted lines) within a period of 10 days. FIG. 6B shows that corresponding insulin bolus injection quantities as a function of time.

The dashed-dotted line of the plot of FIG. 6A shows the open-loop blood glucose concentration as a function of time in the absence of insulin boluses. It can be seen that the glucose levels rise above 200 mg/dl and the patient remains in a hyperglycemic state for an extended period of time.

On day 1, shown by the solid line on FIG. 6B, the initial guesses for the insulin bolus amount and timing can be seen from the plot of insulin injection input for the run-to-run algorithm of FIG. 6A. The corresponding blood glucose concentration still remains outside of the desired boundaries for $G^{max}$ and $G^{min}$ on day one. On day 2, the algorithm continues to compute the optimal insulin bolus amount and timing for each meal, as shown by the dashed line in the plots of FIG. 6A and FIG. 6B. Since $G^{max}$ was largely out of the zone, the timing of the meal bolus changes the most on day 2. Eventually on day 10, represented by the thick solid line, $G^{max}$ and $G^{min}$ for each meal come within the desired bounds.

Finally, a comparison of the performance of the Bergman model with the AIDA and Sorensen virtual patient models was conducted and shown in Table 3. The AIDA model was subject to a 20 g breakfast, 50 g lunch and 65 g dinner. The Sorensen model was subject to a 20 g breakfast, 40 g lunch and 70 g dinner. The target values for the AIDA model were 80 to 140 mg/dl while those for the Sorensen model were 70 to 140 mg/dl. All three models were tuned, without severe oscillations, to converge within a two-week period. Different operating conditions were chosen for each model as the meal and insulin dynamics manifest themselves differently in the glucose profile of each virtual patient model (e.g., subcutaneous versus intravenous administration). Therefore, the settings were chosen so that each model had similar glucose excursions.

Figure 7:
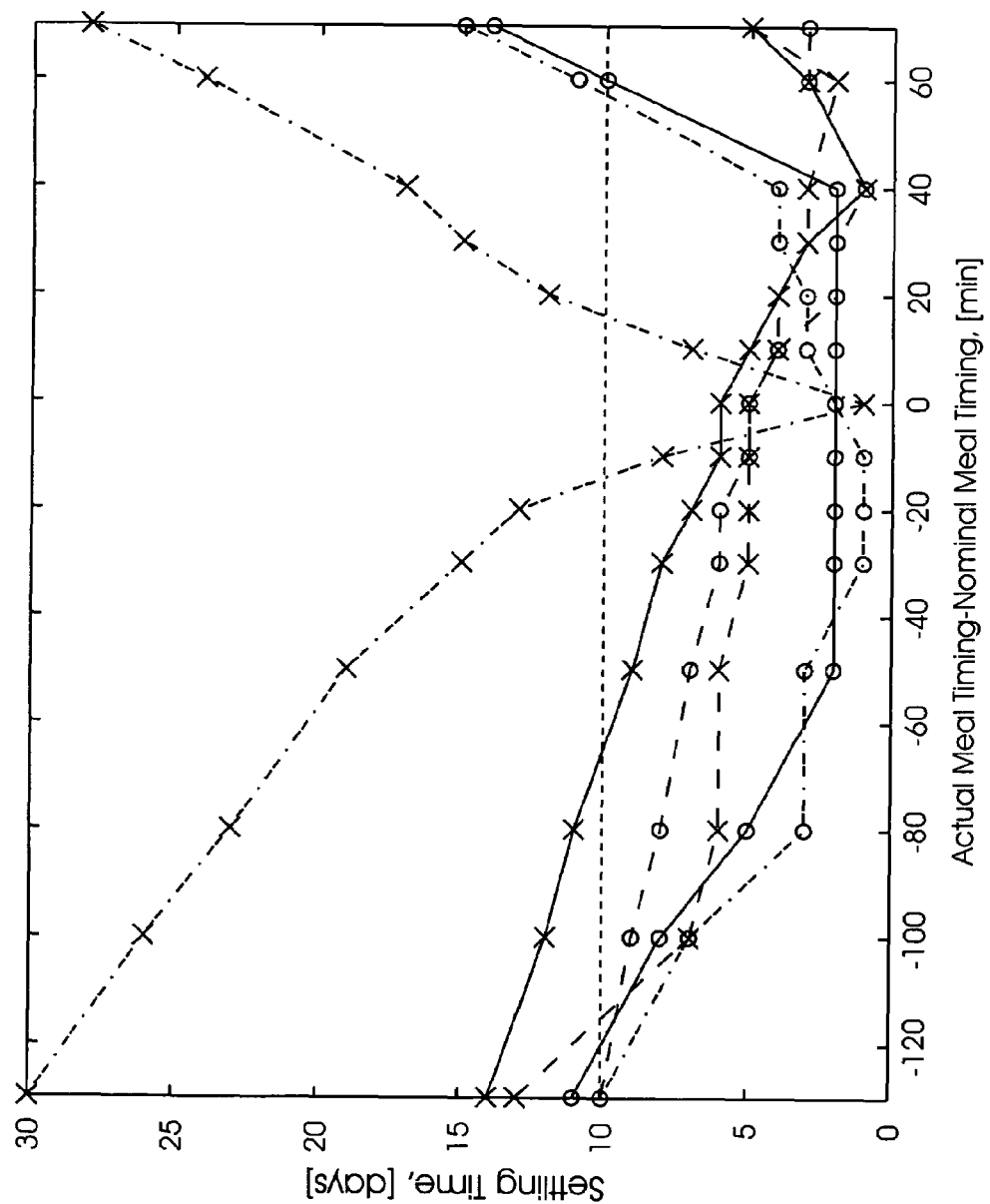
FIG. 7 is a plot of settling time versus variation in meal timing for breakfast, lunch and dinner. The thick dashed line represents the desired window for convergence within 10 days. The (x) represents the maximum blood glucose concentration and the (o) represents the minimum blood glucose concentration. The solid lines denote values for breakfast, values for lunch are denoted by the dotted lines, and values for dinner are denoted by the dashed lines.
Figure 8:
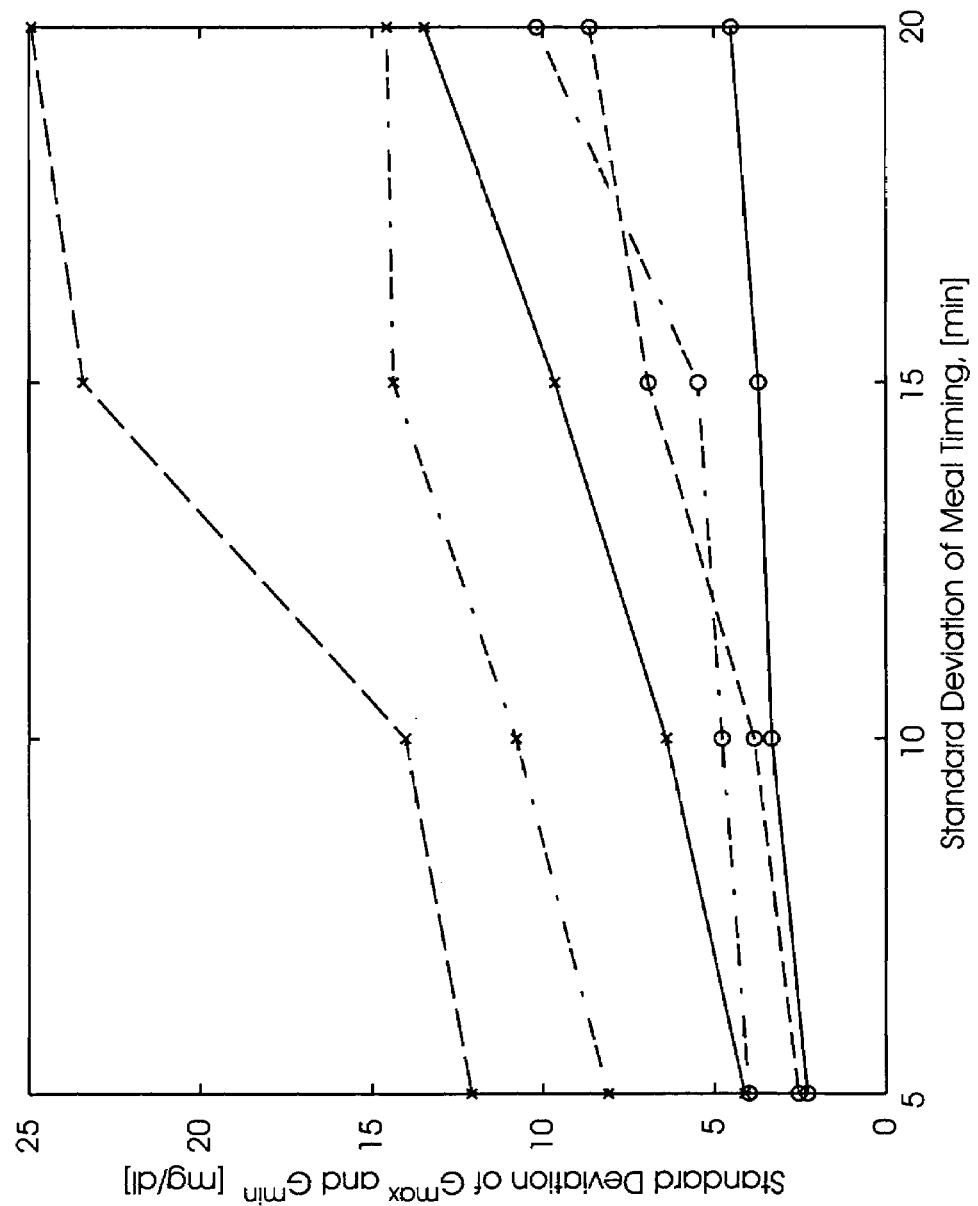
FIG. 8 is a plot of standard deviation of the output variables $G^{max}$ and $G^{min}$ for breakfast, lunch and dinner versus standard deviation in the timing of the meal. The (x) represents the maximum blood glucose concentration and the (o) represents the minimum blood glucose concentration. The solid lines denote values for breakfast, values for lunch are denoted by the dotted lines, and the dashed lines denote values for dinner.

The robustness of the algorithm to variations in the meal amount, meal timing and insulin sensitivity parameters was also evaluated. With regard to meal timing, the algorithm is able to converge when the meal timing is varied within ±40 minutes. Keeping all other variables constant (initial conditions, controller tunings, meal amounts and patient insulin sensitivity), the timing of the meals were simultaneously varied more than ±1 hour from the 8 am, 12 noon, and 5 pm time points for breakfast, lunch and dinner, respectively, as shown in FIG. 7. For all cycles, the deviation in the meal timing remained constant. For variations less than 20 minutes, all meal parameters converge within a window of 5 to 10 days.

Random variations in the meal timing were also introduced from day to day. Random values were selected from a normal distribution that has been truncated to ±3 standard deviations to avoid outliers. Again, all other parameters remained at their nominal values. The standard deviations of the output variables, $G^{max}$ and $G^{min}$, for breakfast, lunch and dinner were calculated as a function of the standard deviation of the variation in the meal timing, shown in FIG. 8. For these simulations, the meal timing was randomly varied from the nominal setting positively and negatively from run to run. As more variation was introduced into the system, the variation in the output variables increased.

Figure 9:
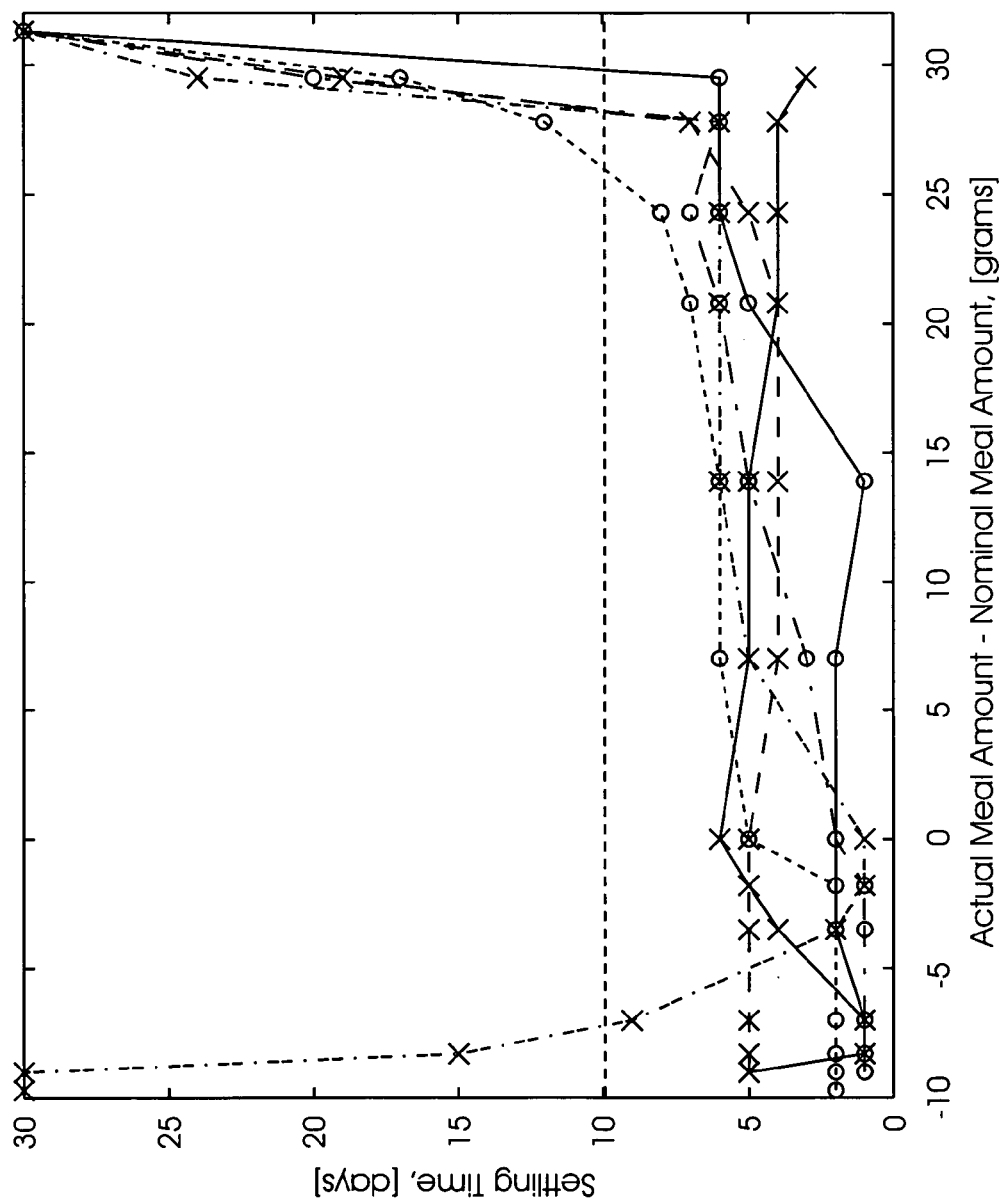
FIG. 9 is a plot of settling time versus variation in meal amount for breakfast, lunch and dinner. The thick dashed line represents the desired window for convergence speed of within 10 days. The (x) represents the maximum blood glucose concentration and the (o) represents the minimum blood glucose concentration. The solid lines denote values for breakfast, values for lunch are denoted by the dotted lines, and values for dinner are denoted by the dashed lines.

Variations in the amount of food consumed at each meal from the nominal values were also analyzed, shown in FIG. 9. It was seen that if the meal size is underestimated by approximately 10 grams, the algorithm is still able to converge within a reasonable time frame for breakfast, lunch and dinner. Similarly, it was seen that the algorithm is also able to converge when the meal size was overestimated up to 20 to 25 grams.

Again, all other settings remained constant to observe the convergence of the algorithm in the presence of variations on the meal amount. For meal amounts approximately 10 grams less than nominal, the algorithm diverges. The initial insulin dosage "over-boluses" the patient and hypoglycemia occurs as the meals become smaller and smaller. Consequently, this moves the timing of the bolus in the other direction (gain change) as $G^{max}$ becomes significantly less than $G^{max,r}$. On the other hand, as the meal gets larger, the initial meal bolus significantly "under doses" the patient but does not change the direction of the bolus timing as $G^{max}$ remains significantly greater than $G^{min,r}$. Once the meal becomes more than 25 to 30 grams larger than nominal, the algorithm begins to diverge. This indicates that there is some flexibility in meal amount that the algorithm can tolerate.

Figure 10:
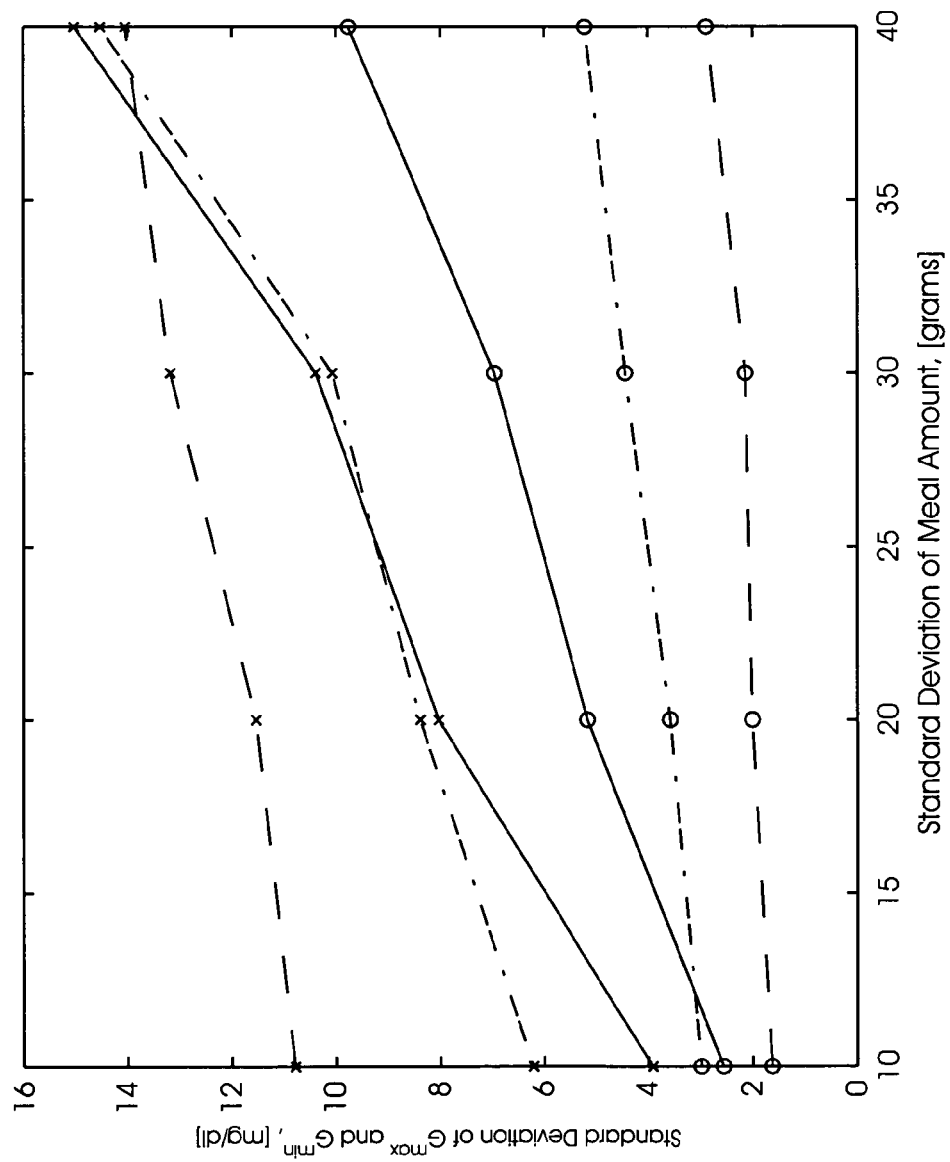
FIG. 10 is a plot of standard deviation of the output variables, $G^{max}$ and $G^{min}$, for breakfast, lunch and dinner versus standard deviation in the amount of the meal. The (x) represents the maximum blood glucose concentration and the (o) represents the minimum blood glucose concentration. The solid lines denote values for breakfast, values for lunch are denoted by the dotted lines, and values for dinner are denoted by the dashed lines.

Random variations in the size of the meal from day to day were also analyzed while keeping all other parameters the same as previously described. FIG. 10 is a plot of the standard deviation of $G^{max}$ and $G^{min}$ as a function of the percent variation in the meal amount. It was observed that as the size of the meal is allowed to randomly vary from ±10% to ±40%, there is a subsequent increase seen in the variation of the output variables. The $G^{max}$ values show the largest variation with dinner being the highest. Again, the trend of increasing variation in output variables with increasing variations introduced into the system is expected.

Accordingly, when random variations in the meal timing and the meal amount are introduced, the variation on the output variables, $G^{max}$ and $G^{min}$, scales according to the amount of variation allowed. Along with this, the insulin sensitivity of the virtual patient model was also varied. During the day and from day-to-day, the typical patient may experience changes in their sensitivity to insulin. In this context, sensitivity refers to the classical biomedical definition, which influences the value of the run-to run sensitivity, (S), described previously.

Figure 11:
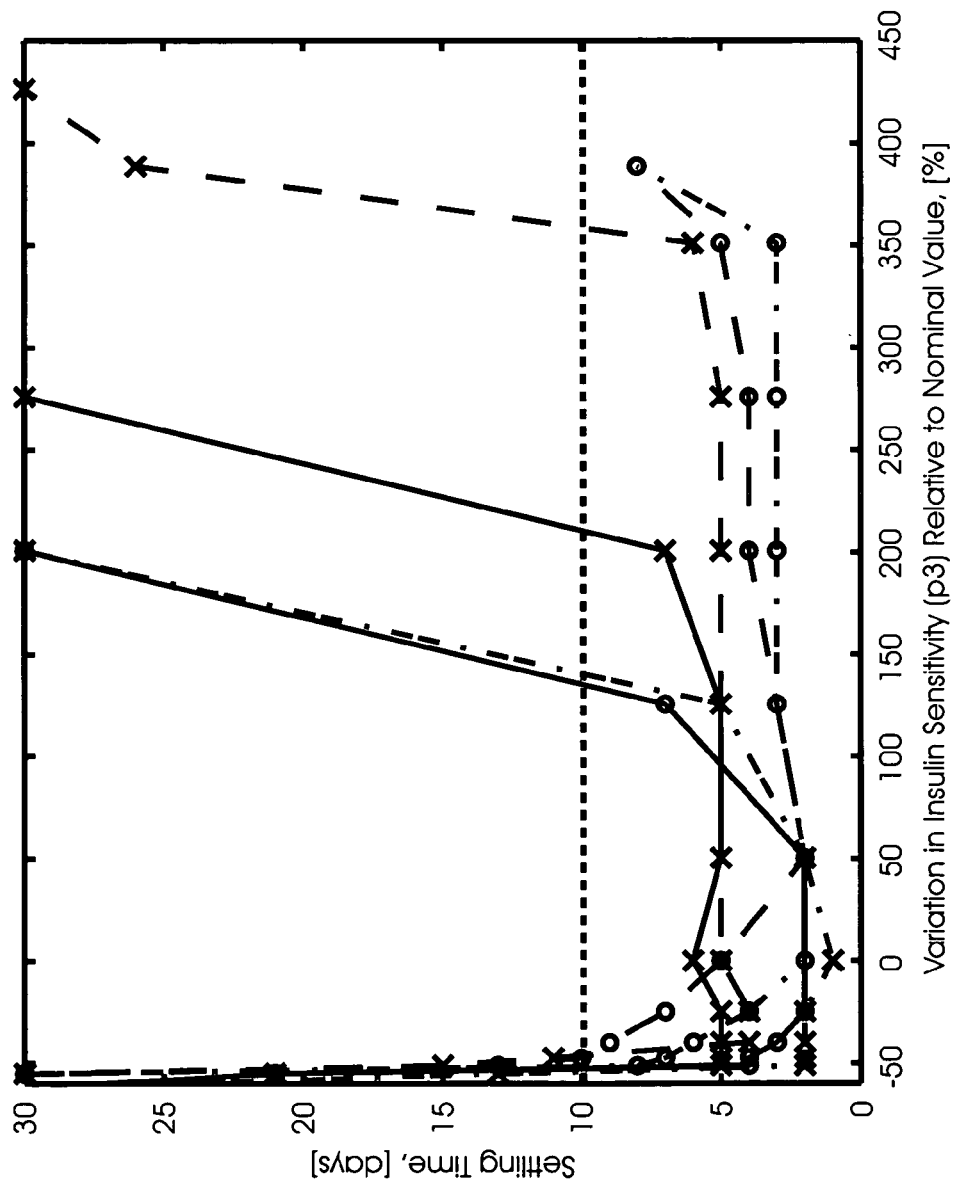
FIG. 11 is a plot of settling time versus variation in insulin sensitivity parameter $p_3$. The thick dashed line represents the desired window for convergence speed of within 10 days. The (x) represents the maximum blood glucose concentration and the (o) represents the minimum blood glucose concentration. The solid lines denote values for breakfast, values for lunch are denoted by the dotted lines, and the dashed lines denote values for dinner.

It can be seen that the speed of convergence may vary as a function of the insulin sensitivity, as shown in FIG. 11. Thirty random realizations of the insulin sensitivity were averaged to generate the results. The extremum values represent the patient becoming highly sensitive to insulin or insensitive to insulin, respectively.

In general, within ±50% of the nominal insulin sensitivity, the algorithm is able to converge within a reasonable time frame. This indicates that the algorithm can tolerate gradual changes in the insulin sensitivity of the patient or mildly abrupt changes in the insulin sensitivity of the individual. As the insulin sensitivity of the patient increases, the insulin has a larger impact on the glucose profile. Consequently, it will continue to converge quickly because the correction in the update laws will get smaller until the initial guess is too much for the meal. Hence, the poles of the error dynamics (I−SK) will be pushed outside of the unit circle. On the other hand, as the insulin sensitivity of the individual decreases with the initial guess, the correction on timing will continue to grow because $G^{max}$ is less affected by the insulin bolus.

These results demonstrate that the run-to-run control algorithm is able to handle day-to-day variations in food intake, time of intake and insulin sensitivity that may occur in a patient with Type 1 diabetes. Moreover, the algorithm aims to properly adjust the current insulin therapy of the individual by trying to make the same decisions as the physician to prescribe appropriate meal insulin doses. With knowledge of the insulin sensitivity of the patient and the appropriate glucose references, the run-to-run control algorithm can help manage diabetes.

EXAMPLE 2

In order to show the feasibility of the use of a run-to-run algorithm to improve postprandial glucose concentrations in individuals with Type 1 diabetes mellitus (T1DM), fourteen subjects were recruited for a 10-week study. During the initial phases of the study, information was derived for each subject with regard to basal insulin infusion rates, insulin-to-carbohydrate ratios, insulin correction factors for hyperglycemia, and insulin sensitivities. During the final phases of the study, the algorithm was used to suggest preprandial insulin doses, with the goal of bringing the postprandial glucose into a predetermined target range within 3-7 days.

Selected participants had a body mass index in the range of 20-30 kg/m2, A1C less than or equal to 8% and ranged in age between 18-75 years. The participants also required 0.5-1.0 units of rapid-acting insulin/kg/day; had serum creatinine levels that were less than or equal to 1.5 mg/dL; exhibited normal laboratory values including thyroid stimulating hormone; and were free from major medical complications.

The study consisted of six discrete phases. Phase 1 consisted of recruitment, informed consent, and adjustment of the basal insulin infusion rates in order to maintain preprandial blood glucose levels between 60 and 120 mg/dL. The total daily insulin dose was initially calculated as 0.6 units/kg/day divided into 50% preprandial insulin infusion and 50% basal insulin infusion. The basal insulin infusion was subdivided into three distinct time periods: 12 a.m. to 4 a.m., 4 a.m. to 10 a.m., and 10 a.m. to 12 midnight. Subjects were asked to skip meals periodically to help fine-tune basal infusion rates.

Phase 2 consisted of a 3-week period in which insulin-to-carbohydrate ratios (the amount of insulin required to cover ingested carbohydrate) and correction factors for hyperglycemia (the amount of insulin required to lower ones blood glucose a defined amount) were derived for each subject.

Each participant was required to record a minimum of 10 finger stick blood glucose measurements per day. For each meal, the subjects were required to check preprandial glucose concentrations, as well as 60 ($G^{60}$) and 90 ($G^{90}$) min postprandial glucose concentrations. A glucose measurement at 3 a.m. was required periodically in order to adjust overnight insulin infusion rates. The subjects sent their blood glucose measurements to the clinic daily after lunch. These data were imported into Camit Pro® software (Roche Diagnostics). Fine adjustments in basal insulin infusions were made during this phase in order to keep preprandial glucose levels between 60 and 120 mg/dL. The desired targets for $G^{60}$ and $G^{90}$ were 160 and 150 mg/dL, respectively.

The participants were also required to adhere to a diet whose caloric content was based on the subject's gender, weight, and physical activity in order to remove the bias of food during the trial. The diet was composed of 30% carbohydrate, 40% fat, and 30% protein. Breakfast consisted of 10% of the total daily calories. Lunch and dinner each consisted 40% of the total daily calories. The remaining 10% was distributed among the three meals as needed. Total calories could range from 20 cal/kg/day for a sedentary female subject to 35 cal/kg/day for a very active male subject. Total daily calories actually ingested in this study population ranged from 24 to 30 cal/kg/day. The meals were tailored to accommodate for food allergies and food preferences. Snacks were only allowed if the subject needed to treat a hypoglycemic event.

Phase 3 consisted of a 3-week period in which the timing and nominal preprandial doses of insulin were perturbed in a prescribed fashion in order to derive insulin sensitivities needed to tune the algorithm. The individual sensitivities of each subject were derived by observing the response of $G^{60}$ and $G^{90}$ to these perturbations. The schedule of perturbations for each subject is shown in Table 4. The negative deviations were −10 min (advance) and −20% (reduce) for the timing and amount, respectively. For example, if the nominal insulin doses for breakfast, lunch, and dinner were 2 U, 3 U, and 4 U of rapid-acting insulin, then the prescription for day 6 of phase 3 would be 2.4 U, 10 min before the start of breakfast, 3 U, 20 min after the start of lunch and 3.6 U, with the start of dinner.

For safety reasons, the 20% positive deviation was decreased as necessary to avoid any overdosing. Each subject had a daily phone consultation with the physician. After a subject sent in his or her blood glucose data, the insulin amount and timing for the following cycle were then prescribed. At the completion of phase 3, the data were analyzed to calculate insulin sensitivities and to see if there were missing data points that could be captured during phase 4.

During phase 4, the individualized insulin sensitivities were refined by repeating a portion of the perturbations in phase 3. This phase lasted 1 week with daily contact with the subjects. For each meal, the $G^{60}$ and $G^{90}$ measurements were only used if the pre-meal blood glucose concentration was within the desired ranges mentioned earlier. At the completion of phase 4, the data were used to determine the insulin sensitivity of each subject.

While these data provide the most ideal source of individual patient sensitivity, additional sources of sensitivity prediction information were also consulted. One additional source included a simulated meal response using the AIDA model tuned to a representative patient response. A third source of patient sensitivity was the medical doctor's estimates, based on the patients responses from phases 1 and 2 as well as their historical insulin-to-carbohydrate ratios. Each patient was assigned a specific insulin sensitivity that reflected a quorum based on the three potential sources of sensitivity data. In cases where the individual measures of patient sensitivity were not in agreement, the doctor's estimates were employed.

Phase 5 consisted of a 1-week period in which the individually tuned algorithm was allowed to provide its recommendations for the following day's timing and amount of bolus insulin for a single meal each day (lunch) based the current day's blood glucose results. On the first day of phase 5, the subject's meal-related insulin dose was decreased by 20% for lunch, and the dose was to be given 20 minutes after the start of the meal. This change in dosage was performed in order to cause postprandial hyperglycemia.

This allowed the algorithm a chance to give suggested dosage amounts and timing changes in order to bring the subjects back into the desired postprandial range. If the subject did not experience postprandial hyperglycemia after the preprandial dose was reduced, the algorithm, by design, would suggest repeating the same pre-meal insulin dosage.

During phase 5, the objective was to allow the aforementioned algorithm to prescribe the timing and amount of the insulin bolus for the lunch meal only. Several modifications were necessary to adhere to the safety guidelines and recommendations of the physicians. First, the controller pairings were switched such that the timing of the insulin bolus affected $G^{90}$ and the amount of the insulin bolus affected $G^{60}$. The reference values for $G^{60}$ and $G^{90}$ was set at 160 mg/dl and 150 mg/dl, respectively. The algorithm made suggestions when $G^{60}$ and $G^{90}$ were outside of the acceptable range of 60-160 mg/dL. Along with this, it was expected that if the bolus was correct then $G^{90}$ should be less than $G^{60}$. If this was not the case, then a correction for $G^{90}$ was provided. Second, it was also decided that if $G^{90}$ was out of range then the timing of the bolus would move in the direction of $G^{60}$. The following equations show a simplified version of the update laws for the amount of the insulin bolus, Q, and the timing of the insulin bolus, T:

$$Q(k+1)=Q(k)+k_Q(G_{ref}^{60}-G^{60})$$

$$T(k+1)=T(k)+k_T(G_{ref}^{90}-G^{90})$$

where k represents the current day, and $G_{ref}^{60}$ and $G_{ref}^{90}$ represent the reference values for $G^{60}$ and $G^{90}$, respectively.

This equation does not reflect the "dead zone" of 60-160 mg/dL, in which no corrective action is taken. The initial conditions for the start of the algorithm were for the patients to take 20% less of their optimal bolus amount, 20 minutes after the start of the meal. This was prescribed to pull the patients out of control so that the algorithm would have the chance to bring them within the desired bounds.

Table 5 lists the controller tunings for the lunch meal, $k_T$ and $k_Q$, for all nine patients. These tuning values were obtained by assigning a 3-4 day response time for the closed-loop patient response, based on individual patient's sensitivity.

Phase 6 consisted of a 1-week period in which the individually tuned algorithm was allowed to give its recommendations for the following day's timing and dosage of pre-meal insulin for all three meals based on the current day's blood glucose results. The initial conditions for this phase were changed such that on the first day of phase 6 the subject would take 25% less of his or her nominal meal-related insulin amount at the start of the meal in order to cause postprandial hyperglycemia. During phases 5 and 6, the physician was required to confirm or override the algorithm's recommendation before the algorithmic derived dose of insulin was prescribed. In the case of an override, the physician would provide his or her own recommendation to the subject. During phase 6, the run-to-run algorithm was implemented on all three meals. In this phase of the study, the controller input-output pairing were switched such that the timing of the insulin bolus was corrected if $G^{60}$ was out of range and the amount of the insulin bolus would be corrected when $G^{90}$ was out of range. This was done to test the response of the $G^{60}$ and $G^{90}$ measurements to the dominant control input, the size of the bolus.

Referring to Table 6, the controller gains for phase 5 and phase 6 for all three meals were determined by evaluation over a 3 or 4 day response time and factored in patient sensitivity. The timing control loop for breakfast, lunch, and dinner for the participants had the same controller tuning value. However, if $G^{60}$ was out of range, the timing of the bolus was moved towards the start of the meal. The breakfast meal control loops for the amount were significantly detuned in comparison with lunch and dinner. This helped to minimize the potential that the patient became out of control for breakfast and consequently had a deleterious impact on the rest of the day's data.

In another embodiment, the phase 5 for the single meal and phase 6 for the three meal update law for the bolus quantity was determined by the following equations, respectively:

$$Q(i+1) = Q(i) + K_Q \begin{bmatrix} \min(G_{60} - 60, 0) - 100 + \max \\ (G_{60} - 150, 0) + 100 \frac{\max(G_{60} - 60, 0)}{\max(G_{60} - 60, \varepsilon)} \end{bmatrix}$$

$$Q(i+1) = Q(i) + K_Q \begin{bmatrix} \min(G_{90} - 60, 0) - 15 + \max \\ (G_{90} - 150, 0) + 15 \frac{\max(G_{90} - 60, 0)}{\max(G_{90} - 60, \varepsilon)} \end{bmatrix}$$

where $K_Q$ is the controller gain $Q(i+1)$ is the new amount of insulin and $Q(i)$ is the old amount of insulin. Epsilon, $\varepsilon$, is a small value used for numerical precision.

Figure 12:
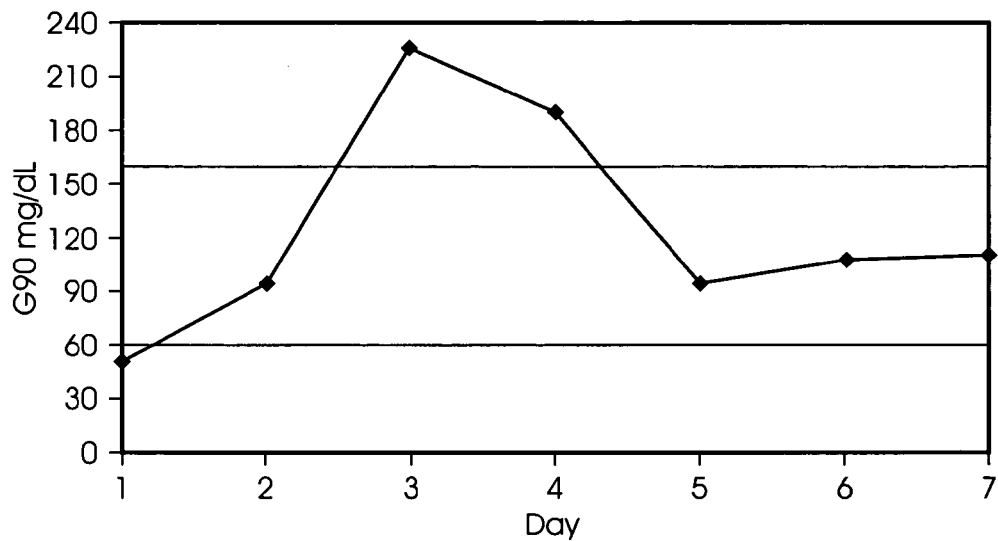
FIG. 12 is a graph showing phase 5 convergence results for subject 2. The dashed lines represent the desired postprandial target zone boundaries of 60 and 160 mg/dl. The convergence classification was A.
Figure 13:
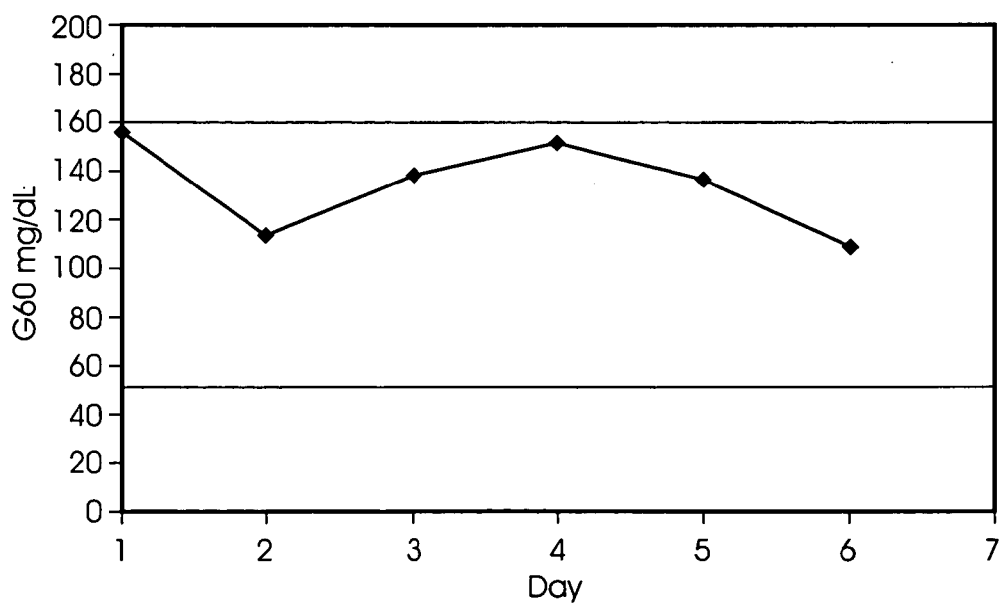
FIG. 13 is a graph showing phase 5 convergence results for subject 5. The dashed lines represent the desired postprandial glucose target zone boundaries of 60 and 160 mg/dl. The convergence classification was B.
Figure 14:
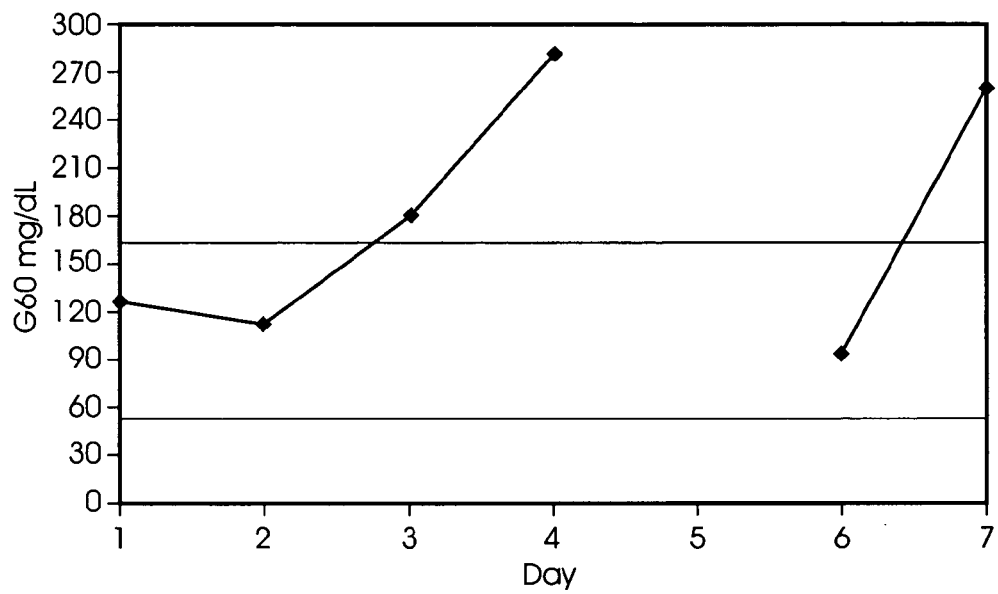
FIG. 14 is a graph showing phase 5 convergence results for subject 9. The dashed lines represent the desired postprandial target zone boundaries of 60 and 160 mg/dl. The convergence classification was C, or divergent.

The convergence results of phases 5 and 6 were separated into three categories for each meal:
1. Class A: Convergent in 3-4 days within target range
2. Class B: Remained in target range
3. Class C: Divergent from target range Phase 5 convergence results for each subject are shown in Table 7. FIG. 12 through FIG. 14 show exemplary phase 5 convergence results for three different subjects, referring to the same meal, each representing a different convergence classification. The dashed lines in FIGS. 12-14 represent the desired postprandial target zone boundaries of 60 and 160 mg/dL.

Figure 15A:
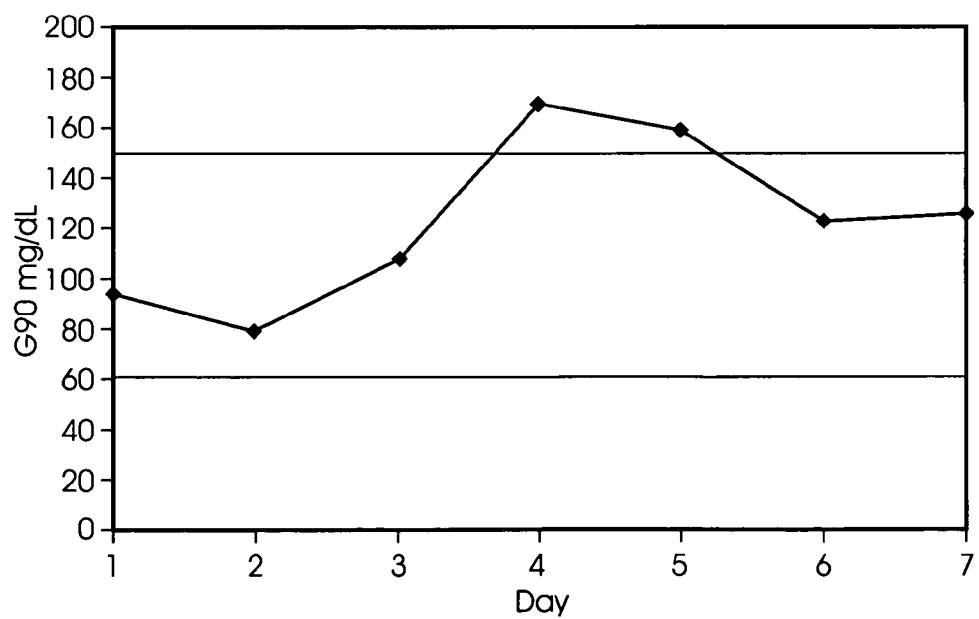
FIG. 15A-C are graphs showing phase 6 convergence results for subject 6. The dashed lines represent the desired postprandial glucose target zone boundaries of 60 and 150 mg/dl. 15A: Breakfast meal with a convergence classification of A. 15B: Lunch meal with a convergence classification of B. 15C: Dinner meal with a convergence classification of C, or divergent.
Figure 15B:
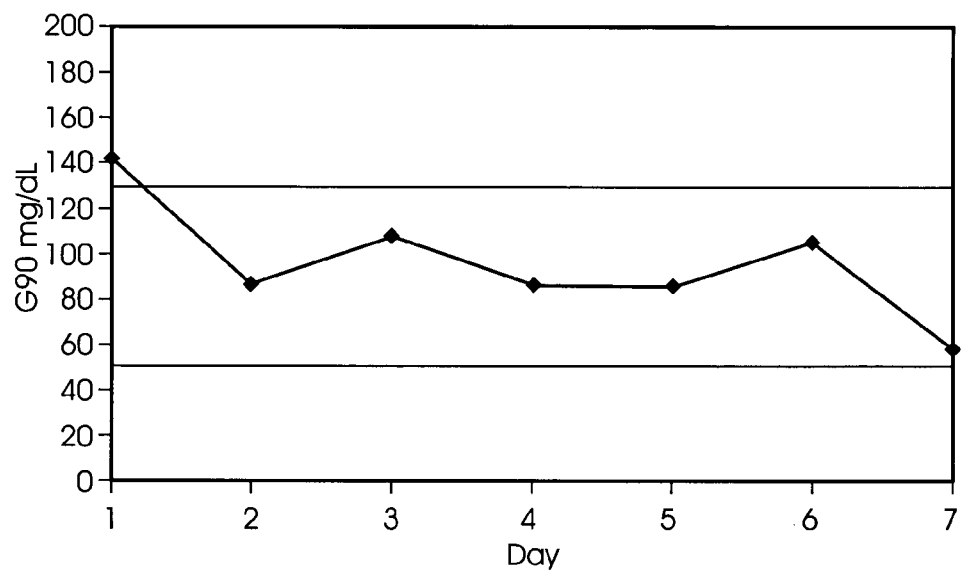
Figure 15C:
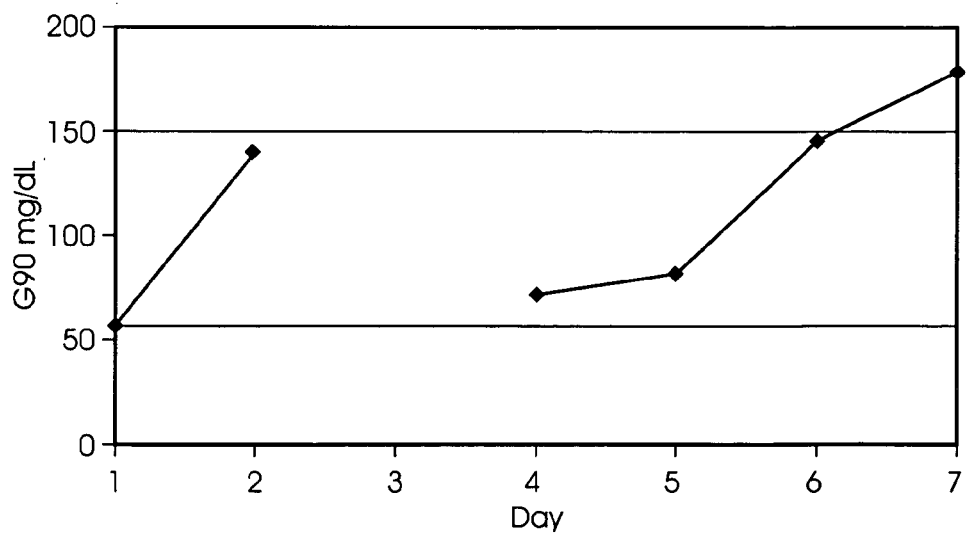
Figure 16:
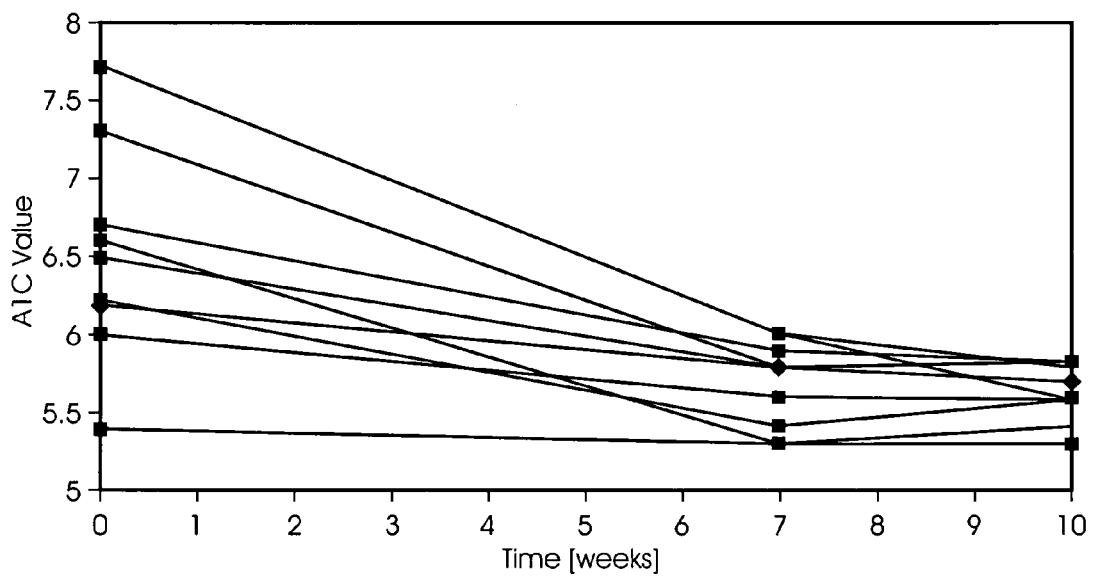
FIG. 16 is a plot of A1C values for the nine subjects who completed the study. All of the subjects had an improvement in his or her A1C percentage from an initial A1C of 6.5±0.7% to an end-of-study A1C of 5.6±0.2% (P<0.003). A1C values were checked at weeks 0, 7, and 10.

Phase 6 convergence results for each subject, by meal, are shown in Table 8. FIGS. 15-16 are exemplary phase 6 convergence results for one subject, showing each of the three meals, each representing a different convergence classification. The dashed lines in FIGS. 15A, 15B and 15C represent the desired postprandial target zone boundaries of 60 and 150 mg/dl.

The convergence results for each subject reflect the algorithm's ability to maintain blood glucose levels $G^{60}$ and $G^{90}$ between the desired boundaries by prescribing the proper insulin bolus amount and timing. In the single-meal phase (phase 5), 33% of the subject-meal responses were convergent in 3-4 days to a clinically acceptable range (A), 33% were always in range, and 33% had divergent responses, incorrect sensitivities, and/or other mitigating circumstances.

In the three-meal phase (phase 6), 41% of the subject-meal responses were convergent in 3-4 days to a clinically acceptable range, 26% were always in range, and 33% had divergent responses, incorrect sensitivities, and/or other mitigating circumstances.

In addition, physician overrides were infrequent during phases 5 and 6, occurring on 10 out of a possible 216 occasions. The initial design was to base the individual insulin sensitivities on data generated during phases 3 and 4. Therefore, the insulin sensitivities used to tune the algorithm for each subject were derived using a combination of subject data, AIDA modeling, and physician input in this trial.

Overall we were able to safely demonstrate that run-to-run modeling can be used to manage meal-related insulin in subjects with Type 1 diabetes on a regulated diet. It was also observed that once the subjects had good postprandial glucose control, it was difficult to cause postprandial hyperglycemia by reducing their meal-related insulin dosage by 20-25%.

FIG. 16 is a plot of the A1C values of each subject during the study. By the end of the 10-week trial, each of the subjects had an improvement in his or her A1C percentage from an initial A1C of 6.5±0.7% to an end-of-study A1C of 5.6±0.2% (P<0.003). This improvement in A1C is most likely a result of the intensive insulin management and daily patient contact, despite frequent intentional underbolusing of their meal-related insulin.

EXAMPLE 3

Another non-limiting example of a run-to-run algorithm correlates the post meal blood glucose (BG) values to a pre-meal carbohydrate intake level. The post meal BG values are sampled at two fiducial lag times relative to the start of the meal at 60 minute and 90 minute time points. To realize a high correlation between a given pre-meal event and the post meal events, the pre-meal event needs specification in two areas: timing and blood glucose level. In this embodiment, the pre-meal carbohydrate intake event is preferably sufficiently isolated in time. It is preferred that in advance of the pre-meal carbohydrate-intake event, no fast-acting insulin bolus must have occurred for an interval of at least 2 hours. If this condition is satisfied, then a "candidate" pre-meal event is identified.

Following a candidate pre-meal carbohydrate intake event, additional carbohydrate-intake events cannot occur more than 20 minutes after the candidate pre-meal carbohydrate intake event. If this condition is satisfied, then the summate of the pre-meal carbohydrate-intake event and all additional carbohydrate-intake events within the 20 minute forgiveness window form an "effective" pre-meal carbohydrate intake event.

It is also preferred that the pre-meal event be accompanied by a blood glucose value within the target range. Violation of any of these conditions may naturally occur. In those cases, a high correlation between pre-meal and post meal may not be found. In this situation, the data pairs (pre-meal and post meal) must be "masked out" or removed as input to the Run-to-Run algorithm. Attempts to use a pre-meal blood glucose value below the target range may lead to anti-correlation.

Accordingly, it can be seen that the apparatus and methods of the invention can derive both the optimal dosage of insulin to provide the basal insulin requirement (that dose of insulin that maintains normal blood glucose levels when there is no food ingested) and the meal-related insulin dosing of an individual, comprising estimating a preprandial dosage of insulin for a subsequent day's corresponding meal based on the observed postprandial glucose response to the meal and preprandial dose of insulin for a current day. The insulin need is predicted for a subsequent day's preprandial insulin dosages through corrections based on a previous day's meal-related postprandial glucose measurements incorporating the variables of time of day (to compensate for the diurnal variation of glucose tolerance), carbohydrate content of the meal, preprandial glucose concentration and time since last meal bolus.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Table of Insulin Sensitivity Values for Virtual Patient Model

| Meal | $s_T = \dfrac{\partial G^{max}}{\partial T}$ [mg/(dl min)] | $s_Q = \dfrac{\partial G^{min}}{\partial Q}$ [mg ml/(dl μU)] |
|---|---|---|
| Breakfast | 0.38 | −1.3E−5 |
| Lunch | 0.38 | −3.43E−6 |
| Dinner | 0.39 | −1.0E−6 |

TABLE 2

Table of Controller Gains for Virtual Patient Model

| Meal | $k_T$ [(min dl)/mg] | $k_Q$ [(μU dl)/mg ml] |
|---|---|---|
| Breakfast | 0.6 | −6.0E4 |
| Lunch | 0.13 | −5.7E4 |
| Dinner | 0.35 | −1.0E5 |

TABLE 3

Table of Model Comparison of Settling Time

| Virtual Patient | $G^{min,r}$, [mg/dl] | $G^{max,r}$, [mg/dl] | Settling Time, [days] |
|---|---|---|---|
| Bergman | 90 | 140 | 7 |
| Sorensen | 70 | 140 | 7 |
| AIDA | 80 | 140 | 9 |

TABLE 4

Phase 3 Perturbations of Nominal Insulin Amounts and Timing

| Day | Breakfast Amount | Breakfast Time | Lunch Amount | Lunch Time | Dinner Amount | Dinner Time |
|---|---|---|---|---|---|---|
| 1  | ○ | ○ | ○ | − | + | ○ |
| 2  | ○ | + | − | ○ | ○ | + |
| 3  | ○ | − | ○ | ○ | + | − |
| 4  | + | ○ | + | − | − | − |
| 5  | + | + | − | − | ○ | − |
| 6  | + | − | ○ | + | − | ○ |
| 7  | − | ○ | + | + | − | + |
| 8  | − | + | + | ○ | ○ | ○ |
| 9  | − | − | − | + | + | + |
| 10 | ○ | − | ○ | ○ | + | − |
| 11 | − | − | − | + | + | + |
| 12 | + | + | − | − | ○ | − |
| 13 | ○ | ○ | ○ | − | + | ○ |
| 14 | + | − | ○ | + | − | ○ |
| 15 | − | + | + | ○ | ○ | ○ |
| 16 | ○ | + | − | ○ | ○ | + |
| 17 | − | ○ | + | + | − | + |
| 18 | + | ○ | + | − | − | − |
| 19 | ○ | + | ○ | − | ○ | + |
| 20 | − | ○ | + | ○ | − | ○ |
| 21 | + | ○ | ○ | + | ○ | − |

○ represents the nominal insulin amount and timing defined during phases 1 and 2,
+ represents the positive deviations for the amount and timing of the insulin bolus, and
− represents the negative deviations for the amount and timing of the insulin bolus for each meal.

TABLE 5

Controller Gains for Phase 5

| Subject number | $-1/k_T$ | $-1/k_Q$ |
|---|---|---|
| 1 | 7.9 | 35.0 |
| 2 | 8.0 | 13.5 |
| 3 | 11.8 | 20.0 |
| 4 | 13.0 | 19.0 |
| 5 | 11.6 | 25.0 |
| 6 | 17.0 | 12.0 |
| 7 | 6.4 | 10.0 |
| 8 | 7.0 | 12.0 |
| 9 | 7.2 | 15.3 |

Units of $k_T$ are U/(mg/dL), and units of $k_Q$ are min/(mg/dL)].

TABLE 6

Controller Gains for Phase 6

| Subject number | $-1/k_T$ | $-1/k_Q$ Breakfast | Lunch | Dinner |
|---|---|---|---|---|
| 1 | 12.0 | 105 | 70.0 | 70.0 |
| 2 | 12.0 | 40.5 | 27.0 | 27.0 |
| 3 | 18.0 | 60.0 | 40.0 | 40.0 |
| 4 | 19.5 | 57.0 | 38.0 | 38.0 |
| 5 | 17.4 | 75.0 | 50.0 | 50.0 |
| 6 | 25.5 | 36.0 | 24.0 | 24.0 |
| 7 | 9.6 | 30.0 | 20.0 | 20.0 |
| 8 | 10.5 | 36.0 | 24.0 | 24.0 |
| 9 | 10.8 | 45.9 | 30.6 | 30.6 |

Units of $k_T$ are U/(mg/dL), and units of $k_Q$ are min/(mg/dL)].

TABLE 7

Convergence Results for Phase 5

| Subject number | Convergence class |
|---|---|
| Subject 1 | B |
| Subject 2 | A |
| Subject 3 | A |
| Subject 4 | B |
| Subject 5 | B |
| Subject 6 | A |
| Subject 7 | C |
| Subject 8 | C |
| Subject 9 | C |

Class A, convergent in 3–4 days within target range;
Class B, always within the clinically adequate range;
Class C, divergent from target range.

TABLE 8

Convergence Results for Phase 6

| Subject number | Convergence class | | |
|---|---|---|---|
| | Breakfast | Lunch | Dinner |
| Subject 1 | B | B | B |
| Subject 2 | C | C | A |
| Subject 3 | B | A | B |
| Subject 4 | A | C | C |
| Subject 5 | A | B | A |
| Subject 6 | C | A | B |
| Subject 7 | A | A | A |
| Subject 8 | A | C | C |
| Subject 9 | C | C | A |

Class A, convergent in 3–4 days within target range;
Class B, always within the clinically adequate range;
Class C, divergent from target range.

What is claimed is:

1. A run-to-run control method of deriving the optimal dosage of insulin to provide both the basal insulin requirement and the meal-related insulin dosing of an individual having diabetes, comprising:
    determining an insulin sensitivity matrix for said individual;
    measuring a postprandial glucose response to at least one meal; and
    estimating a preprandial dosage of insulin for a subsequent cycle's corresponding meal based on said insulin sensitivity matrix of said individual and measured postprandial glucose response to the meal and preprandial dose of insulin for a current cycle;
    wherein each element of said insulin sensitivity matrix is a function of one or more parameters affecting insulin needs of an individual pertaining to said individual;
    wherein said one or more parameters is selected from the group consisting of physical stress, psychological stress, hormonal stress, activity, fitness, and weight;
    wherein said insulin sensitivity matrix reflects a breadth of output responses in said individual as a function of changes in input; and
    wherein dosage amount for a subsequent cycle is higher than, lower than, or the same as, dosage amount for a current cycle.

2. A method as recited in claim 1, wherein said insulin dosage comprises an insulin analog.

3. A method as recited in claim 1, wherein said dosage further comprises timing of said dosage of insulin.

4. A method as recited in claim 1, wherein maximum glucose levels following each meal are maintained within the normal glycemic range.

5. A method as recited in claim 1, wherein a subsequent cycle's preprandial insulin dosages are corrected based on one or more meal-related postprandial glucose measurements from a previous cycle.

6. A method as recited in claim 5, wherein said dosage corrections incorporate at least one of the variables of time of day, carbohydrate content of a meal, preprandial glucose concentration and time since last meal bolus.

7. A method as recited in claim 1, further comprising:
    repeating said estimating step through successive cycles until glucose levels converge to a predetermined target range.

8. A method as recited in claim 1, further comprising:
    (a) measuring blood glucose level during a current cycle;
    (b) estimating insulin dosage for said subsequent cycle as a function of said measured blood glucose level during said current cycle;
    (c) administering said insulin dosage based on said estimate; and
repeating steps (a) through (c).

9. A method as recited in claim 1, wherein a cycle comprises a twenty-four hour period during which meals are ingested at variable times during the period.

10. A method as recited in claim 9, wherein more than three meals are ingested during the cycle.

11. A method as recited in claim 9, wherein fewer than three meals are ingested during the cycle.

12. A method as recited in claim 3, wherein said timing and amount of said insulin dosages provide an insulin dosing profile that is optimized over time.

13. A method as recited in claim 1, wherein said measuring step comprises at least one measurement of blood glucose levels from a sensor taken from the group of sensors consisting essentially of an implanted glucose sensor, an optical glucose sensor and a pin prick glucose sensor.

14. A method as recited in claim 13, wherein said parameter pertaining to said individual is selected from the group consisting of an exercise level and a degree of stress.

15. A method as recited in claim 14, wherein said exercise level parameter has mild, moderate or strenuous exercise levels.

16. A method as recited in claim 14, wherein said degree of stress parameter has mild, moderate or severe stress levels.

17. A method as recited in claim 1, wherein said estimating step is a function of said blood glucose level measurement, meal size and meal timing.

18. A method as recited in claim 1, wherein said estimating step is a function of said blood glucose level measurement, meal size, carbohydrate content, meal timing, and meal duration.

19. A method as recited in claim 18, wherein said parameter pertaining to said individual is selected from the group of stresses consisting essentially of physical stress, psychological stress or hormonal stress.

20. A method as recited in claim 1, wherein the preprandial dosage of insulin for a subsequent cycle's meal is iteratively updated over time.

21. A method as recited in claim 20, wherein said dosage comprises insulin amount and timing of delivery.

* * * * *